United States Patent [19]
Proxmire et al.

[11] Patent Number: 5,192,606
[45] Date of Patent: Mar. 9, 1993

[54] ABSORBENT ARTICLE HAVING A LINER WHICH EXHIBITS IMPROVED SOFTNESS AND DRYNESS, AND PROVIDES FOR RAPID UPTAKE OF LIQUID

[75] Inventors: Deborah L. Proxmire, Larsen, Wis.; Wanda W. Jackson, Alpharetta, Ga.; Nancy D. Kollin, Roswell, Ga.; Tamara L. Mace, Alpharetta, Ga.; Ann L. McCormack, Cumming, Ga.; Daniel R. Schlinz, Appleton, Wis.

[73] Assignee: Kimberly-Clark Corporation, Neenah, Wis.

[21] Appl. No.: 757,778

[22] Filed: Sep. 11, 1991

[51] Int. Cl.⁵ .................. B32B 5/06; D04H 1/00; A61F 13/15; A61F 13/20
[52] U.S. Cl. .................. 428/284; 428/913; 428/273; 428/237; 428/298; 604/378
[58] Field of Search .................. 604/378; 428/284, 913

[56] References Cited

U.S. PATENT DOCUMENTS

| | | | |
|---|---|---|---|
| 2,761,449 | 9/1956 | Bletzinger | 128/285 |
| 3,016,599 | 1/1962 | Perry | 28/78 |
| 3,308,826 | 3/1967 | Blake | 128/290 |
| 3,369,544 | 2/1968 | Crockford | 128/285 |
| 3,523,536 | 8/1970 | Ruffo | 128/287 |
| 3,592,194 | 7/1971 | Duncan | 128/287 |
| 3,595,235 | 7/1971 | Jespersen | 128/284 |
| 3,612,055 | 10/1971 | Mesek et al. | 128/287 |
| 3,663,348 | 5/1972 | Liloia et al. | 161/116 |
| 3,665,921 | 5/1972 | Stumpf | 128/287 |
| 3,730,184 | 5/1973 | Mesek | 128/287 |
| 3,768,118 | 10/1973 | Ruffo et al. | 19/156.3 |
| 3,768,480 | 10/1973 | Mesek et al. | 128/287 |
| 3,772,417 | 11/1973 | Vogt | 264/230 |
| 3,777,758 | 12/1973 | Mesek | 128/284 |
| 3,806,289 | 4/1974 | Schwarz | 425/72 |
| 3,837,343 | 9/1974 | Mesek | 128/287 |
| 3,871,378 | 3/1975 | Duncan et al. | 128/290 |
| 3,908,659 | 9/1975 | Wehrmeyer et al. | 128/287 |
| 3,927,673 | 12/1975 | Taylor | 128/287 |
| 3,945,386 | 3/1976 | Anczurowski et al. | 128/287 |
| 3,952,124 | 4/1976 | Mesek | 428/218 |
| 3,965,905 | 6/1976 | Schoenholz et al. | 128/285 |
| 3,965,906 | 6/1976 | Karami | 128/287 |
| 3,978,185 | 8/1976 | Buntin et al. | 264/93 |
| 3,987,792 | 10/1976 | Hernandez et al. | 128/284 |
| 4,014,341 | 3/1977 | Karami | 128/287 |
| 4,018,862 | 4/1977 | Saito | 264/137 |
| 4,041,951 | 8/1977 | Sanford | 128/287 |
| 4,044,768 | 8/1977 | Mesek et al. | 128/287 |
| 4,045,833 | 9/1977 | Mesek et al. | 5/335 |
| 4,077,410 | 3/1978 | Butterworth et al. | 128/287 |
| 4,103,058 | 7/1978 | Humlicek | 428/171 |
| 4,118,531 | 10/1978 | Hauser | 428/224 |

(List continued on next page.)

FOREIGN PATENT DOCUMENTS

0070163 1/1983 European Pat. Off. .
0070164 1/1983 European Pat. Off. .

(List continued on next page.)

*Primary Examiner*—Jenna L. Davis
*Assistant Examiner*—Chris Raimund
*Attorney, Agent, or Firm*—Paul Yee

[57] ABSTRACT

A distinctive absorbent article includes a backsheet layer which has a width dimension and a length dimension, and which includes a front waistband section, a back waistband section, and an intermediate section interconnecting the front and back waistband sections. An absorbent body is superposed on the backsheet layer, and an intermediate transfer layer, which is liquid permeable, is disposed in facing relation with the absorbent body to generally sandwich the absorbent body between the backsheet and transfer layer. The transfer layer has an appointed bodyside, inner surface, and a bodyside liner layer is located on the inner surface of the transfer layer. The bodyside liner comprises a bonded carded web which has a basis weight within the range of about 15-40 gsm and is composed of bicomponent fibers having a fiber denier within the range of about 1.0-3.0 dpf. The bodyside liner is constructed to provide for a Penetration rate index of at least about 1.5 ml/sec and a Retention index of not more than about 0.8 gm.

49 Claims, 18 Drawing Sheets

U.S. PATENT DOCUMENTS

| | | | |
|---|---|---|---|
| 4,212,302 | 7/1980 | Karami | 128/287 |
| 4,216,772 | 8/1980 | Tsuchiya et al. | 128/284 |
| 4,223,677 | 9/1980 | Anderson | 128/287 |
| 4,232,674 | 11/1980 | Melican | 128/287 |
| 4,238,175 | 12/1980 | Fujii et al. | 425/83.1 |
| 4,259,958 | 4/1981 | Goodbar | 128/287 |
| 4,285,342 | 8/1981 | Mesek | 128/287 |
| 4,304,234 | 12/1981 | Hartmann | 128/287 |
| 4,324,247 | 4/1982 | Aziz | 128/287 |
| 4,338,371 | 7/1982 | Dawn et al. | 428/283 |
| 4,364,992 | 12/1982 | Ito et al. | 428/283 |
| 4,372,312 | 2/1983 | Fendler et al. | 128/290 R |
| 4,374,888 | 2/1983 | Bornslaeger | 428/198 |
| 4,381,611 | 5/1983 | Wishman | 34/9 |
| 4,381,782 | 5/1983 | Mazurak et al. | 604/368 |
| 4,392,861 | 7/1983 | Butterworth et al. | 604/366 |
| 4,392,862 | 7/1983 | Marsan et al. | 604/366 |
| 4,397,644 | 8/1983 | Matthews et al. | 604/378 |
| 4,405,325 | 9/1983 | Antlfinger et al. | 604/370 |
| 4,413,032 | 11/1983 | Hartmann et al. | 428/288 |
| 4,421,813 | 12/1983 | Athey | 428/195 |
| 4,436,780 | 3/1984 | Hotchkiss et al. | 428/198 |
| 4,461,621 | 7/1984 | Karami et al. | 604/368 |
| 4,468,428 | 8/1984 | Early et al. | 428/221 |
| 4,480,000 | 10/1984 | Watanabe et al. | 428/284 |
| 4,496,358 | 1/1985 | Karami et al. | 604/379 |
| 4,500,315 | 2/1985 | Pieniak et al. | 604/366 |
| 4,500,384 | 2/1985 | Tomioka et al. | 156/290 |
| 4,501,586 | 2/1985 | Holtman | 604/380 |
| 4,519,798 | 5/1985 | Dinius | 604/358 |
| 4,519,799 | 5/1985 | Sakurai et al. | 604/366 |
| 4,531,945 | 7/1985 | Allison | 604/378 |
| 4,535,020 | 8/1985 | Thomas et al. | 428/131 |
| 4,537,590 | 8/1985 | Pieniak et al. | 604/379 |
| 4,540,414 | 9/1985 | Wishman | 604/378 |
| 4,540,454 | 9/1985 | Pieniak et al. | 156/62.2 |
| 4,550,725 | 11/1985 | Wishman | 128/155 |
| 4,551,143 | 11/1985 | Cook et al. | 604/371 |
| 4,552,603 | 11/1985 | Harris, Jr. et al. | 156/167 |
| 4,559,051 | 12/1985 | Hanson | 604/385 R |
| 4,560,372 | 12/1985 | Pieniak | 604/369 |
| 4,573,988 | 3/1986 | Pieniak et al. | 604/379 |
| 4,578,066 | 3/1986 | O'Connor | 604/366 |
| 4,578,070 | 3/1986 | Holtman | 604/378 |
| 4,578,414 | 3/1986 | Sawyer et al. | 524/310 |
| 4,590,114 | 5/1986 | Holtman | 428/171 |
| 4,608,292 | 8/1986 | Lassen | 428/131 |
| 4,623,340 | 11/1986 | Luceri | 604/385 R |
| 4,623,576 | 11/1986 | Lloyd et al. | 428/171 |
| 4,636,209 | 1/1987 | Lassen | 604/378 |
| 4,654,040 | 3/1987 | Luceri | 604/385 R |
| 4,655,757 | 4/1987 | McFarland et al. | 604/366 |
| 4,673,402 | 6/1987 | Weisman et al. | 604/368 |
| 4,675,013 | 6/1987 | Ruffo | 604/366 |
| 4,681,577 | 7/1987 | Stern et al. | 604/378 |
| 4,699,619 | 10/1987 | Bernardin | 604/378 |
| 4,699,620 | 10/1987 | Bernardin | 604/385 A |
| 4,704,112 | 11/1987 | Suzuki et al. | 604/378 |
| 4,707,398 | 11/1987 | Boggs | 428/224 |
| 4,714,647 | 12/1987 | Shipp, Jr. et al. | 428/212 |
| 4,732,809 | 3/1988 | Harris, Jr. et al. | 428/373 |
| 4,735,624 | 4/1988 | Mazars | 604/378 |
| 4,738,676 | 4/1988 | Osborn, III | 604/385 R |
| 4,755,178 | 7/1988 | Insley et al. | 604/367 |
| 4,755,179 | 7/1988 | Shiba et al. | 604/370 |
| 4,794,034 | 12/1988 | Nishizawa et al. | 428/218 |
| 4,798,603 | 1/1989 | Meyer et al. | 604/378 |
| 4,830,904 | 5/1989 | Gessner et al. | 428/219 |
| 4,851,284 | 7/1989 | Yamanoi et al. | 428/284 |
| 4,883,707 | 11/1989 | Newkirk | 428/219 |
| 4,923,454 | 5/1990 | Seymour et al. | 604/368 |
| 4,988,344 | 1/1991 | Reising et al. | 604/368 |
| 4,988,345 | 1/1991 | Reising | 604/368 |

FOREIGN PATENT DOCUMENTS

| | | |
|---|---|---|
| 0108637 | 5/1984 | European Pat. Off. |
| 0165807 | 12/1985 | European Pat. Off. |
| 0174775 | 3/1986 | European Pat. Off. |
| 0193309A1 | 9/1986 | European Pat. Off. |
| 0254476 | 1/1988 | European Pat. Off. |
| 0317058A1 | 5/1989 | European Pat. Off. |
| 0377212A2 | 7/1990 | European Pat. Off. |
| 3525379A1 | 1/1987 | Fed. Rep. of Germany |
| 61-2854 | 1/1986 | Japan |
| WO80/01455 | 7/1980 | PCT Int'l Appl. |
| WO86/05661 | 9/1985 | PCT Int'l Appl. |
| 1308935 | 3/1973 | United Kingdom |
| 1389891 | 4/1975 | United Kingdom |
| 1402327 | 8/1975 | United Kingdom |
| 1547524 | 6/1979 | United Kingdom |
| 2023068 | 12/1979 | United Kingdom |
| 2055586A | 3/1981 | United Kingdom |
| 2063683A | 6/1981 | United Kingdom |
| 2087240A | 5/1982 | United Kingdom |
| 2089214A | 6/1982 | United Kingdom |
| 2101038 | 1/1983 | United Kingdom |
| 2101038A | 1/1983 | United Kingdom |
| 2131699A | 6/1984 | United Kingdom |
| 2145661A | 4/1985 | United Kingdom |
| 2170108A | 7/1986 | United Kingdom |
| 2214201A | 8/1989 | United Kingdom |

TABLE 1

| Sample No. | | 9 | 10 | 11 | 12 | 13 | 14 |
|---|---|---|---|---|---|---|---|
| Fiber Denier | dpf | 1.80 | 1.80 | 3.00 | 1.97 | 2.49 | 2.58 |
| Basis Weight | osy | 0.80 | 0.80 | 0.80 | 0.72 | 0.93 | 0.89 |
| Thickness (.1 psi) | in. | 0.045 | 0.030 | 0.012 | 0.008 | 0.035 | 0.033 |
| Density | g/cc | 0.019 | 0.021 | 0.037 | 0.073 | 0.044 | 0.025 |
| MD tensile | lb/in | 4.39 | 3.91 | | | | |
| CD tensile | lb/in | 0.96 | 0.45 | | | | |
| MD/CD ratio | | 4.57 | 8.69 | 1.80 | 2.80 | 3.00 | 3.33 |
| Bulk at: | | | | | | | |
| .1 psi (dry) | in. | 0.045 | 0.030 | 0.008 | 0.009 | 0.035 | 0.029 |
| .1 psi (wet) | in. | | 0.034 | 0.007 | 0.011 | 0.039 | 0.034 |
| 1.0 psi (dry) | in. | 0.019 | 0.010 | 0.006 | 0.005 | 0.013 | 0.011 |
| 1.0 psi (wet) | in. | | 0.010 | 0.006 | 0.007 | 0.015 | 0.008 |
| Rec. at .1 psi (dry) | % | 56.00 | 50.00 | 72.73 | 77.78 | 60.00 | 44.83 |
| Rec. at .1 psi (wet) | % | | 32.35 | 70.00 | 63.64 | 46.15 | 38.24 |

FIG. 12A

TABLE 1 (Continued)

| Sample No. | 9 | 10 | 11 | 12 | 13 | 14 |
|---|---|---|---|---|---|---|
| Kawabata: | | | | | | |
| B(MD) | 0.84 | 0.05 | 0.02 | | | |
| B(CD) | 0.15 | | 0.04 | | | |
| G(MD) | 1.02 | 1.11 | 1.53 | | | |
| G(CD) | 0.87 | 1.55 | 2.09 | | | |
| MIU(MD) | 0.29 | 0.22 | 0.19 | | | |
| MIU(CD) | 0.31 | 0.23 | 0.20 | | | |
| SMD(MD) | 1.70 | 2.62 | 4.21 | | | |
| SMD(CD) | 4.07 | 4.54 | 4.50 | | | |
| TO | 2.21 | 2.64 | 0.47 | 0.63 | | 2.05 |
| TM | 0.91 | 0.35 | 0.33 | 0.31 | | 0.59 |
| RC | 48.42 | 49.22 | 63.18 | 46.52 | | 53.59 |

FIG. 12B

TABLE 2

| Sample No. | | 9 | 10 | 11 | 12 | 13 | 14 |
|---|---|---|---|---|---|---|---|
| FIFE Rate | ml/sec | 2.65 | 2.42 | 0.88 | 2.07 | 3.00 | 2.32 |
| Flowback | gms. | 0.49 | 0.16 | 0.36 | 6.80 | 1.53 | 3.47 |
| Retention | gms. | | 0.46 | 0.30 | 0.43 | 1.62 | 1.84 |
| Desorption Ratio | | 99.00 | 90.85 | 38.00 | 50.05 | 40.67 | 91.30 |

FIG. 13

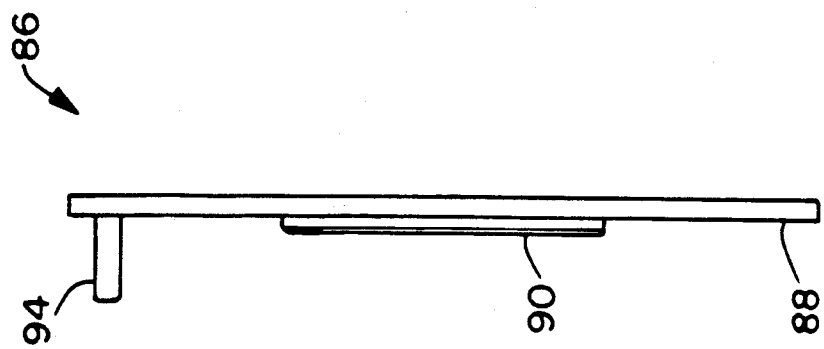
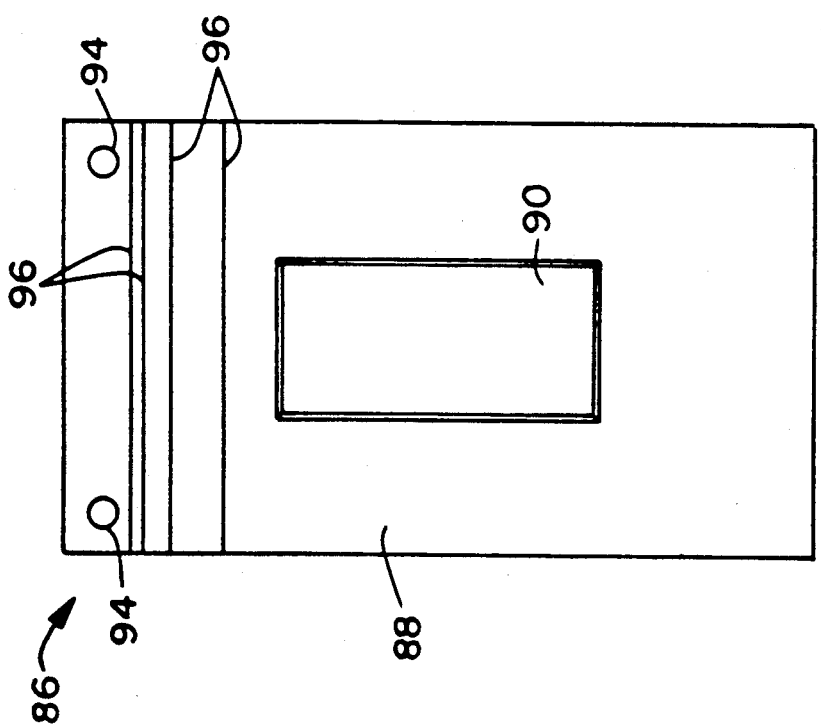

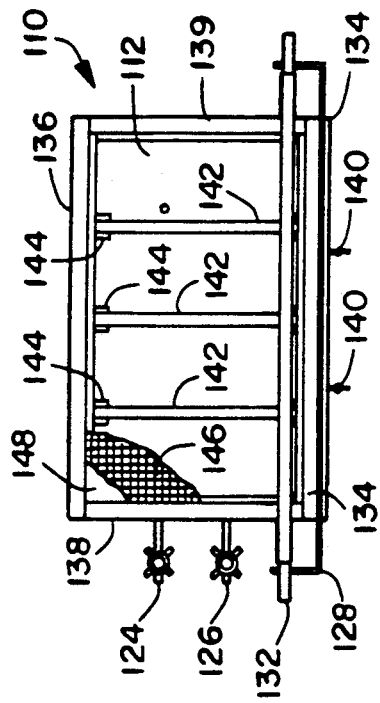
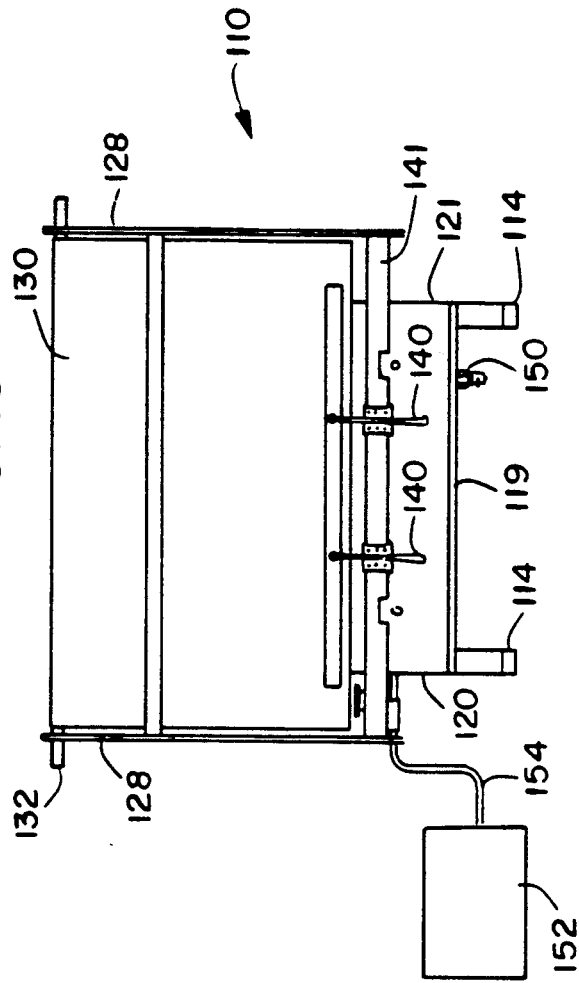
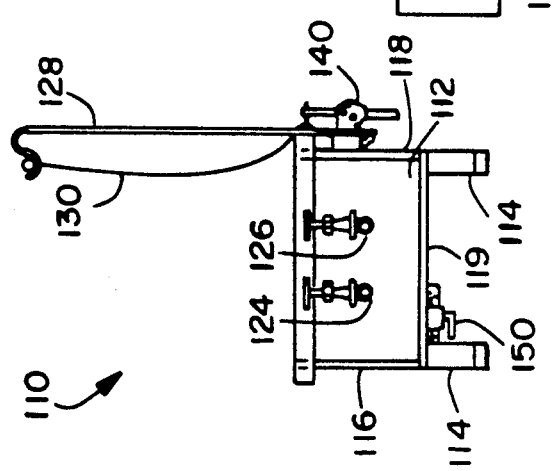

_5,192,606_

ABSORBENT ARTICLE HAVING A LINER WHICH EXHIBITS IMPROVED SOFTNESS AND DRYNESS, AND PROVIDES FOR RAPID UPTAKE OF LIQUID

TECHNICAL FIELD

This invention relates to absorbent articles, particularly absorbent structures which are useful in personal care products. More particularly, the invention relates to absorbent articles which have a portion designed for rapid uptake, and subsequent release of repeated liquid surges to the remainder of the article.

BACKGROUND OF THE INVENTION

Desired performance objectives of personal care absorbent products include low leakage from the product and a dry feel to the wearer. However, absorbent products commonly fail before the total absorbent capacity of the product is utilized. An absorbent garment, for example a disposable diaper, often leaks at the leg, top front or top back areas of the diaper. Leakage can occur due to a variety of shortcomings in the product, one being an insufficient rate of fluid uptake by the absorbent system, especially on the second, third or fourth liquid surges.

It has been found that urination can occur at rates as high as 15 to 20 milliliters per second and at velocities as high as 280 centimeters per second. Conventional diaper absorbent structures, such as those comprising admixtures of absorbent gelling particles and cellulosic fluffed pulp, may initially uptake fluid at rates of only about 8 milliliters per second or less, depending somewhat on the web density and concentration of gelling particulates. Even the rates for these fabrics can deteriorate once they have already received liquid surges into their structures. The above disparity between liquid delivery and uptake rates can result in excessive pooling on the surface of the fabric before it is taken up by the structure. In the meantime, pooled fluid can wet the wearer's skin, leak from the leg opening of the diaper and soil the outer clothing or bedding of the wearer.

Attempts to alleviate leakage include providing physical barriers with elastic leg gathers and changing the amount or configuration of the absorbent material at the zone of the structure into which the liquid surges typically occur. Absorbent gelling particles have also been included to increase the liquid holding capacity in various regions of the absorbent structure.

Absorbent articles have typically employed various types of absorbent pads composed of cellulosic fibers. For example, U.S. Pat. No. 3,523,536 to Ruffo discloses an absorbent fibrous web of predominantly shorter fibers intermixed with relatively longer fibers for purposes of stabilizing the web. U.S. Pat. No. 3,768,118 to Ruffo, et al. relates to a process for blending longer and shorter fibers. U.S. Pat. No. 3,663,348 to Liloia, et al. discloses an absorbent product in which a disclosed fabric serves as a body side, fluid pervious liner material, and an absorbent core includes a loosely compacted cellulose batt with a densified layer on one side.

Particular absorbent garments have been configured to control the distribution of absorbed liquids. U. S. Pat. No. 4,578,070 to Holtman discloses incontinence pads which include a bilayer, corrugated nonwoven structure. U.S. Pat. No. 4,681,577 to Stern and Holtman discloses incontinence pads placed in a liquid-impermeable, flexible shell. The absorbent structure disclosed in the '577 patent includes either a corrugated or uncorrugated version of the bilayer nonwoven structure disclosed in the '070 patent, located in the front portion of the product. A second resilient, open structure, such as a resilient nonwoven or open cell foam, in the back portion is further disclosed for the purpose of providing fecal waste containment.

U.S. Pat. No. 4,699,619 to Bernardin discloses a cellulosic absorbent structure which can comprise a multi-layer core arrangement wherein a top layer has a greater pore size than that of an underlying layer. The pore size gradient between the core layers can be achieved in various ways, for example, by using webs of different densities or webs with a common density but formed from fibers of different sizes. A portion of superabsorbent material can also be placed at various locations within the absorbent structure.

U.S. Pat. No. 4,585,448 issued Apr. 29, 1986 to K. Enloe describes a disposable garment comprising an integral absorbent pad disposed between a liquid pervious body-side liner sheet and a liquid impervious backing sheet. The absorbent pad is provided with a high absorbency area extending from the crotch region toward the center of the front waist of the garment. It is preferred that about 65 percent of the total absorbent be in the front half of the diaper with about 40 percent of the total in the high absorbency area. The higher zones of absorbency can alternatively be formed by use of zoned superabsorbent materials.

U.S. Pat. No. 4,798,603 issued Jan. 17, 1989 to S. Meyer et al. describes an absorbent article including an absorbent body composed of a substantially hydrophilic material which is capable of absorbing a selected liquid. A liquid permeable transfer layer composed of a substantially hydrophobic material is superposed in facing relation with an absorbent body, and has an effective average pore size therein. A liquid permeable transport layer is located between the transfer layer and the absorbent body, and is composed of a material which is less hydrophilic than the absorbent body. The transport layer has an effective average pore size therein which is smaller than the pore size of the transfer layer.

European Application No. 254,476 and U.S. Pat. No. 4,834,735 of Alemany et al. disclose an absorbent member having fluid storage and acquisition zones composed of cellulosic fluff mixed with absorbent gelling particles. The particles are purportedly used to keep the fibrous structure from collapsing when wet. The acquisition zone has a lower density and lower basis weight than that of the storage zone. U.S. Pat. No. 4,673,402 to Weisman, et al. discloses a dual-layer absorbent core arrangement comprising a bottom fluff pad containing hydrogel particles, and a top fluff pad with little or no hydrogel particles.

Non-woven materials such as carded webs and spun-bonded webs, have been used as the body-side liners in absorbent products. Specifically, very open, porous liner structures have been employed to allow liquid to pass through them rapidly, and help keep the body skin separated from the wetted absorbent pad underneath the liner. In addition other layers of material, such as those constructed with thick, lofty fabric structures, have been interposed between the liner and absorbent pad for the purpose of reducing wet-back.

With conventional fluff-based absorbent structures, such as those discussed above, the cellulosic fibers, when wetted, can lose resiliency and collapse. As a result, the liquid uptake rate of the wetted structures may become too low to adequately accommodate subsequent, successive liquid surges. Where absorbent gelling particles are incorporated between the fibers to hold them apart, the gelling particles swell and do not release the absorbed fluid. Swelling of the particles can then diminish the void volume of the absorbent structure and reduce the ability of the structure to rapidly uptake liquid.

The addition of more absorbent material, e.g., secondary fluff pledgets or absorbent gelling particles, has been employed to increase holding capacity. The desired rate of liquid intake within such arrangements, however, may not be sufficiently sustained during successive liquid surges.

Despite the development of absorbent structures of the types surveyed above, there remains a need for improved absorbent structures which can adequately reduce the incidence of leakage from absorbent products, such as disposable diapers. There is a need for an absorbent structure which can provide improved handling of liquid surges and more effectively uptake and retain repeated loadings of liquid during use.

BRIEF DESCRIPTION OF THE INVENTION

A distinctive absorbent article includes a backsheet layer which has a width dimension and a length dimension, and which includes a front waistband section, a back waistband section, and an intermediate section interconnecting the front and back waistband sections. An absorbent body is superposed on the backsheet layer, and an intermediate transfer layer, which is liquid permeable, is disposed in facing relation with the absorbent body to generally sandwich the absorbent body between the backsheet and transfer layer. The transfer layer has an appointed bodyside, inner surface, and a bodyside liner layer is located on the inner surface of the transfer layer. The bodyside liner comprises a bonded carded web which has a basis weight within the range of about 15–40 gsm and is composed of bicomponent fibers having a fiber denier within the range of about 1.0–3.0 dpf. The bodyside liner is constructed to provide for a Penetration rate index of at least about 1.5 ml/sec and a Retention index of not more than about 0.8 gm.

The absorbent structure of the present invention advantageously provides a bodyside liner which can provide for a rapid uptake body exudates and can maintain the rate of uptake even after the absorbent structure has been previously wetted with one or more liquid insults. The invention can also provide a transitional, limited-time reservoir for temporarily containing each liquid surge occurring in the target zone of the absorbent structure, and can further provide a more complete release and movement of the liquid into a retention portion of the structure. As a result, a garment which includes the distinctive arrangements of the present invention can help avoid puddling of liquid against the wearer's skin, and more rapidly move the liquid away from the skin and into the absorbent structure. The transitional reservoir function of the invention can advantageously allow the retention portion a greater period of time in which to accept repeated surges of liquid while also isolating the liquid away from the wearer's skin. The more complete release of the liquid into the retention portion helps to maintain a dryer section of the garment against the wearer. Thus, the distinctive structure of the present invention can reduce the amount of liquid held against the wearer's skin, reduce leakage of liquid from the absorbent structure, and provide improved dryness and comfort to the wearer. In addition, the features of the present invention can be advantageously sustained during the course of multiple insults of liquid delivered into the absorbent article. The improved bodyside liner can also provide improved softness and can help reduce skin irritation or abrasion. Where the bodyside liner material extends to the end edges of the diaper, the liner material can help provide a gentler, softer waistband which can reduce red marks. The bodyside liner can have high bulk, compression resiliency, and improved uniformity. The uniform appearance of the body side liner material can enhance the consumer perception of dryness since the soiled diaper can better retain an "unused" appearance. The body side liner material can also have improved durability and exhibit reduced pilling and linting during use.

BRIEF DESCRIPTION OF THE DRAWINGS

The invention will be more fully understood and further advantages will become apparent when reference is made to the following detailed description and accompanying drawings in which:

FIG. 12A and 12B is a Table summarizing fabric data for Examples 9-14;

FIG. 13 is a Table summarizing performance data for Examples 9-14;

FIGS. 14A-4B representatively show a top view and a side view, respectively, of the bottom base board employed for the Forced Intake and Flowback Evaluation testing;

FIGS. 18A, 18B, and 18C representatively show a partially cut away top view, a side view and a rear view, respectively, of a Saturated Capacity tester.

DETAILED DESCRIPTION OF THE INVENTION

The absorbent structures of the present invention will be described herein in relationship to their use in disposable absorbent articles, but it should be understood that potential uses of the absorbent structures of the present invention need not be limited to disposable absorbent articles. As used herein, the term "disposable absorbent article" refers to articles which absorb and contain body exudates and are intended to be discarded after a limited period of use. They are not intended to be laundered or otherwise restored for reuse. The articles can be placed against or in proximity to the body of the wearer to absorb and contain various exudates discharged from the body. While the present description will particularly be made in the context of a diaper article, it should be understood that the present invention is also applicable to other disposable personal care absorbent articles, such as children's training pants, adult incontinence garments, sanitary napkins, and the like, as well as surgical bandages and sponges.

Figure 1A:
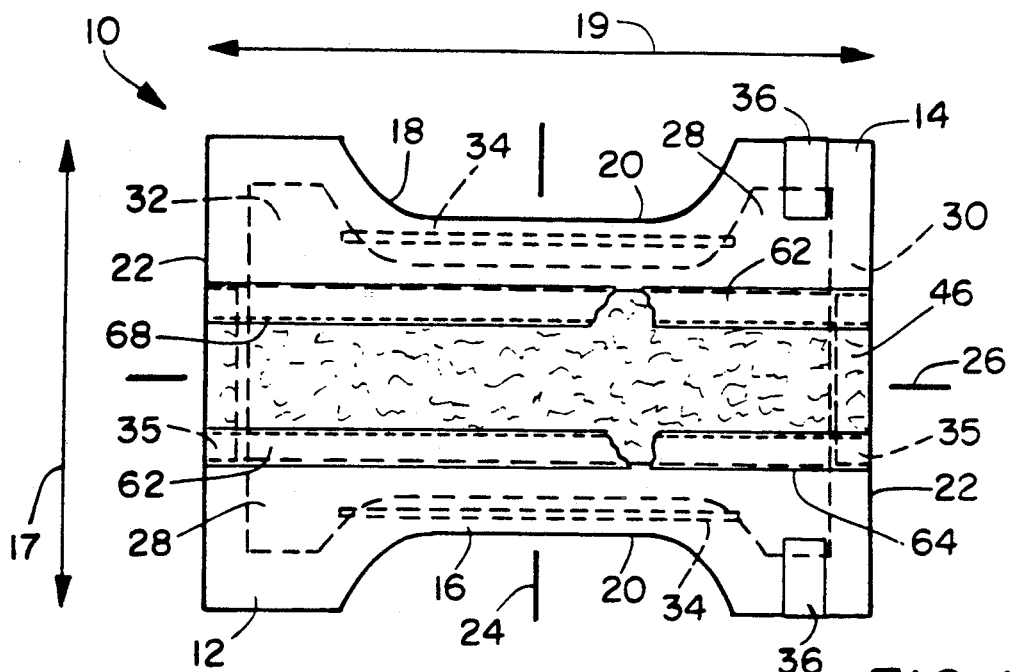
FIG. 1A representatively shows a partially cut away, top plan view of an embodiment of the invention, wherein the bodyside liner is positioned between the attached edges of a pair of internal containment flaps.
Figure 1B:
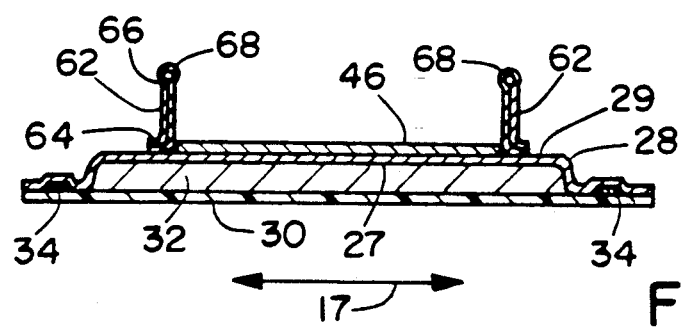
FIG. 1B representatively shows a lateral cross-sectional view of the article of FIG. 1A, wherein the elastic members at the distal edges of the containment flaps have urged sections of the flaps to a generally upright position, spaced away from the bodyside liner.
Figure 1C:
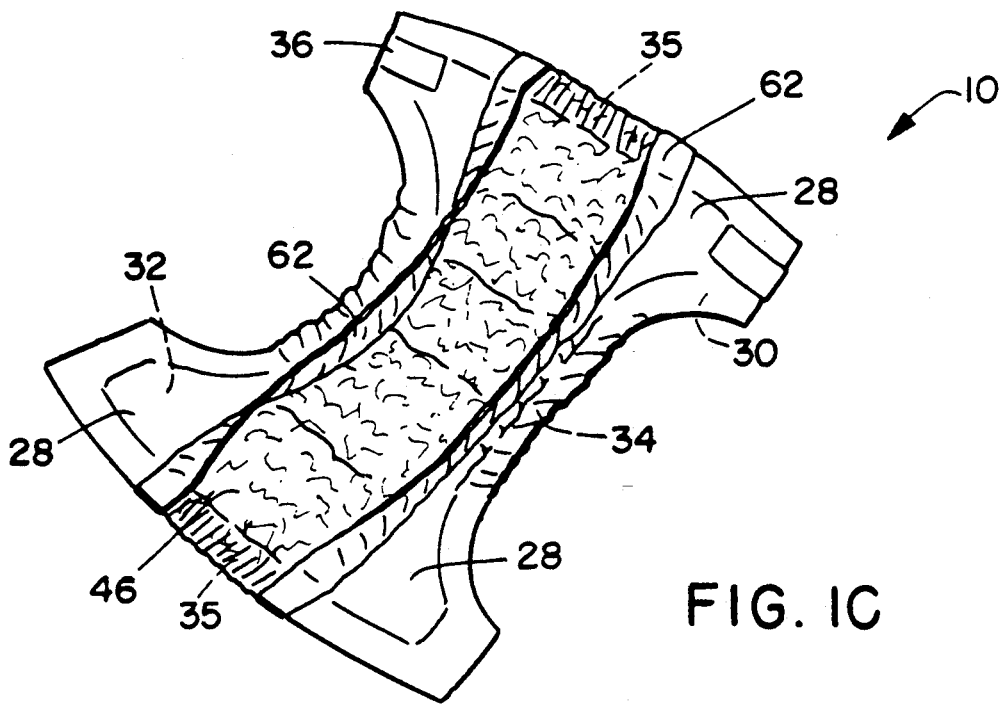
FIG. 1C representatively shows a perspective view of the article of FIG. 1A, wherein the leg elastics and flap elastics have contracted and gathered the side margins of the article and the distal edges of the containment flaps.

Referring to FIGS. 1A-1C, an absorbent article, such as diaper 10, includes a backsheet layer 30 which has a width dimension 17 and a length dimension 19, and which defines a front waistband section, a back waistband section, and an intermediate crotch section which interconnects the front and back waistband sections. An absorbent body, such as absorbent structure 32, is superposed on backsheet layer 30, and an intermediate transfer layer 28 composed of liquid permeable material is disposed in facing relation with absorbent body 32 to generally sandwich the absorbent body between backsheet layer 30 and transfer layer 28. The transfer layer has an appointed outer side surface 27 and an appointed bodyside, inner surface 29, and a bodyside liner layer 46 is located on the inner surface of transfer layer 28. In particular configurations of the invention, transfer layer 28 can be configured to provide a combination transfer layer/topsheet structure. Bodyside liner 46 comprises a bonded carded web (BCW) which has a basis weight within the range of about 15-40 gsm and is composed of bicomponent fibers having a fiber denier within the range of about 1.0-3.0 dpf, and the bodyside liner is constructed to provide for a Penetration Rate index of at least about 1.5 ml/sec and a Retention index of not more than about 0.8 gm. In a particular aspect of the invention, the bodyside liner can be constructed to provide for a Penetration Rate index of at least about 1.5 ml/sec and a Flowback index of not more than about 1.2 gm. In yet another aspect of the invention, the bodyside liner can be constructed to provide for a Penetration Rate index of at least about 1.5 ml/sec, a Flowback index of not more than about 2.0 gm, and a Retention index of not more than about 0.8 gm.

FIG. 1A is a representative plan view of diaper 10 in a flat-out, uncontracted state (i.e., with all elastic induced gathering and contraction removed) with the portion of diaper 10 which contacts the wearer facing the viewer. In the shown embodiment, diaper 10 has a front waistband region 12, a back waistband region 14, a crotch region 16, and a periphery 18 which is defined by the outer edges of the diaper, in which the longitudinally extending side edges are designated 20 and the laterally extending end edges are designated 22. Preferably, the side edges are curvilinear and contoured to define leg openings for the diaper. The end edges are shown as straight, but optionally, may be curvilinear. The diaper additionally has a transverse center line 24 and a longitudinal center line 26.

Diaper 10 typically includes component parts, such as transfer layer 28, backsheet 30, absorbent structure 32, and elastic members 34. These components may be assembled into a variety of well-known diaper configurations. It should be recognized, however, that in articles other than diapers, individual components, such as elastic members 34, may be optional. The desirability of including particular components in other absorbent articles would depend upon their intended end use.

In the shown embodiment of diaper 10, intermediate transfer layer 28 and backsheet 30 are substantially coextensive, and have length and width dimensions which are generally larger than those of absorbent structure 32. Transfer layer 28 is associated with and superimposed on backsheet 30, thereby defining a periphery 18 of diaper 10. The periphery delimits the outer perimeter and edges of diaper 10, and comprises end edges 22 and longitudinal edges 20. Thus, diaper 10 defines front and back waistband regions 12 and 14, respectively extending from the end edges 22 of the diaper periphery 18 toward the transverse center line 24 of the diaper a distance from about 2 percent to about 10 percent and preferably about 5 percent of the length of diaper 10. The waistband regions comprise those upper portions of diaper 10, which when worn, wholly or partially cover or encircle the waist or mid-lower torso of the wearer. The intermediate, crotch region 16 lies between and interconnects waistband regions 12 and 14, and comprises that portion of diaper 10 which, when worn, is positioned between the legs of the wearer and covers the lower torso of the wearer. Thus, the crotch region 16 is an area where repeated fluid surge can typically occur in diaper 10 or other disposable absorbent article.

The shown embodiment of intermediate transfer layer 28 presents a body-facing surface which is compliant, soft-feeling, and non-irritating to the wearer's skin. Further, transfer layer 28 comprises a material which is sufficiently porous to be liquid permeable, permitting liquid to readily penetrate through its thickness. A suitable transfer layer 28 may be manufactured from a wide range of web materials, such as porous foams, reticulated foams, apertured plastic films, natural fibers (for example, wood or cotton fibers), synthetic fibers (for example, polyester or polypropylene fibers), or a combination of natural and synthetic fibers. Transfer layer 28 is typically employed to help isolate the wearer's skin from liquids held in absorbent structure 32.

Various woven and nonwoven fabrics can be used for transfer layer 28. For example, the transfer layer may be composed of a meltblown or spunbonded web of polyolefin fibers. The transfer layer may also be a bonded-carded-web composed of natural and/or synthetic fibers. The term "fabrics" is used to refer generally to all woven, knitted and nonwoven fibrous webs. The terms "nonwoven fabric" and "nonwoven web" mean a web of fibrous material which is formed without the aid of a textile weaving or knitting process.

The transfer layer fabric material may be composed of a substantially hydrophobic material, and the hydrophobic material may optionally be treated with a surfactant or otherwise processed to import a desired level of wettability and hydrophilicity. In particular embodiments of the invention, transfer layer 28 is a nonwoven spunbond fabric produced from polypropylene material. The fabric is composed of about 2-5 denier fibers. Preferably, the fiber denier is within the range of about 2.5-4, and more preferably, is within the range of about 2.75-3.5 to provide improved effectiveness. In addition, the fabric forms a web having a basis weight of about 17-51 gsm. Preferably, the web basis weight is within the range of about 19-34 gsm, and more preferably, is within the range of about 20-24 gsm to provide desired benefits. The density of the transfer layer web is about 0.032-0.043 gm/cc. Preferably, the web density is within the range of about 0.033-0.041 gm/cc, and more preferably, is within the range of about 0.035-0.039 gram/cc to provide improved performance. The transfer layer web also includes about 0.11-0.43 weight percent of a suitable surfactant, such as Triton X-102 surfactant available from Rhom & Haas, a company having offices located in Philadelphia, Pa. In preferred embodiments, transfer layer 28 includes about 0.16-0.38 weight percent of surfactant.

In various aspects of the invention, transfer layer 28 may have different configurations. For example, the transfer layer width may be arranged to be coextensive with the width of backsheet 30 over at least a portion of the width of the backsheet intermediate section. Alternatively, the transfer layer width may be arranged to be coextensive with the width of absorbent structure 32 in at least the crotch section of the absorbent structure. In yet other configurations, the transfer layer width may be less than the minimum width of the absorbent structure.

In FIGS. 1A and 1B, the shown embodiment of diaper 10 includes a transfer layer 28 which is substantially coextensive with the total area backsheet 30 and is composed of a nonwoven polypropylene spunbond fabric. The fabric comprises 3 denier polypropylene fibers formed with a fabric basis weight of about 0.7 oz/yd$^2$ (about 24 gsm). Two containment flaps 62 are connected to the bodyside surface of transfer layer 28. Suitable constructions and arrangements for containment flaps 62 are described, for example, in U.S. Pat. No. 4,704,116 issued Nov. 3, 1987, to K. Enloe, the disclosure of which is hereby incorporated by reference to the extent that it is consistent herewith. Bodyside liner 46 is located on an inner, bodyside surface 29 of transfer layer 28, and is positioned between the two containment flaps 62. The bodyside liner is suitably assembled onto transfer layer 28 with conventional attachment means, such as lines or swirled patterns of hot melt adhesive.

Containment flaps 62 are attached to bodyside liner 46 along the fixed edges 64 of the flaps. A movable edge 66 of each containment flap includes a flap elastic member 68 comprising one or more individual strands of elastomeric material. For example, the elastic strands may be in a separated, generally parallel arrangement. Elastic member 68 is connected to the movable edge of the containment flap in an elastically contractible condition such that the contraction of the elastic components thereof gathers and shortens the edge of the containment flap, thereby causing the movable edge of each containment flap to position itself in a spaced relation away from the surface of bodyside liner 46 toward a generally upright configuration. The containment flaps may be constructed of a material which is the same as or different than the material comprising transfer layer 28.

In the various embodiments of the invention, backsheet 30 can be composed of a substantially liquid impermeable material, and is typically manufactured from a thin plastic film, or other flexible liquid-impermeable material. As used in the present specification, the term "flexible" refers to materials which are compliant and which will readily conform to the general shape and contours of the wearer's body. Backsheet 30 prevents the exudates contained in absorbent structure 32 from wetting articles such as bedsheets and overgarments which contact diaper 10. For example, backsheet 30 can be a polyethylene film having a thickness of from about 0.012 millimeters (0.5 mil) to 0.051 millimeters (2.0 mils). Depending upon cost constraints and strength requirements, a typical polyethylene film has a thickness of about 1 mil. Alternative constructions of the backsheet may comprise a woven or nonwoven fibrous web layer which has been constructed or treated to impart the desired level of liquid impermeability.

For example, the backsheet may comprise a polymer film, such as polyethylene film available from Edison Plastics, a business having offices located in South Plainfield, N.J. The polymer film backsheet can also be embossed and/or matte finished to provide a more aesthetically pleasing appearance.

Backsheet 30 may optionally be composed of a vapor permeable, "breathable" material which permits vapors to escape from absorbent structure 32 while still substantially preventing liquid exudates from passing through the backsheet. For example, backsheet 30 can comprise a microporous, polymer film, or a nonwoven fabric which has been coated or otherwise treated to impart desired levels and combinations of liquid impermeability and vapor permeability.

The shape and size of backsheet 30 are determined by the size and contour of absorbent structure 32 and by the particular diaper design selected. Backsheet 30, for example, may have a generally T-shape, a generally I-shape or a modified hourglass shape, and may extend beyond the terminal edges of absorbent structure 32 by a selected distance, e.g., 1.3 centimeters to 2.5 centimeters (0.5 to 1.0 inch).

Transfer layer 28 and backsheet 30 are connected or otherwise associated together in an operable manner. As used therein, the term "associated" encompasses configurations where transfer layer 28 is directly joined to backsheet 30 by affixing marginal areas of transfer layer 28 directly to backsheet 30, and configurations where transfer layer 28 is joined to backsheet 30 by affixing transfer layer 28 to intermediate members which in turn are affixed to backsheet 30. Transfer layer 28 and backsheet 30 can be affixed directly to each other in the diaper periphery 18 by attachment means (not shown) such as an adhesive, sonic bonds, thermal bonds or any other attachment means known in the art. For example, a uniform continuous layer of adhesive, a patterned layer of adhesive, or an array of separate lines, swirls or spots of construction adhesive may be used to affix transfer layer 28 to backsheet 30. It is readily apparent that the above-described attachment means may also be employed to interconnect and assemble together the other component parts of the article.

Fastening means, such as adhesive tape tab fasteners 36, are typically applied to the back waistband region 14 of diaper 10 to provide a mechanism for holding the diaper on the wearer. Tape tab fasteners 36, shown in their inwardly-folded storage position, can be any of those well known in the art, and are typically attached to the corners of diaper 10. The adhesive taping system may be configured to be refastenable, and may include one or more supplemental landing zone patches connected to either the inside or outside surface of the backsheet. For example, see U.S. Pat. No. 4,753,649 to Pazdernik and U.S. Pat. No. 4,296,750 issued Oct. 27, 1981 to Woon et al.. Alternatively, mechanical fasteners, such as belts, hook-and-loop fasteners, mushroom-and-loop fasteners, snaps, pins or buckles, may be used rather than, or in combination with adhesives and other means. It should be understood that is may be possible to dispense with the fasteners in a given design configuration.

Elastic members 34 and 35, if included in the particular article, are disposed adjacent the periphery 18 of diaper 10. Along each longitudinal edge 20, elastic members 34 are arranged to draw and hold the lateral, side margins of diaper 10 against the legs of the wearer. Additionally, elastic members 34 may also be disposed adjacent either or both of the end edges 22 of diaper 10 to provide an elasticized waistband. It should be noted that elasticized leg gathers and waist gathers are typically used in conventional diapers to reduce leakage caused by inadequacies of conventional absorbent structures and materials. In some instances, the present invention may be advantageously configured to lessen reliance on the elasticized gathers for liquid containment purposes.

Elastic members 34 and 35 are secured to diaper 10 in an elastically contractible condition so that in a normal, under-strain configuration, the elastic members effectively contract against and effectively gather portions of diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their unrelaxed or unstretched condition. Still other means, such as heat-shrink elastic material, may be used to gather the garment.

In the embodiment illustrated in FIG. 1A-1C, elastic members 34 extend essentially the length of the crotch region 16 of diaper 10. Alternatively, elastic members 34 may extend the entire length of diaper 10, or any other length suitable providing the arrangement of elastically contractible lines desired for the particular diaper design.

Elastic members 34 may have any of a multitude of configurations. For example, the width of the individual elastic members 34 may be varied from 0.25 millimeters (0.01 inches) to 25 millimeters (1.0 inches) or more; elastic members 34 may comprise a single strand of elastic material or may comprise several parallel or non-parallel strands of elastic material; or may be applied in a rectilinear or curvilinear arrangement. Elastic members 34 may be affixed to the diaper in any of several ways which are known in the art. For example, elastic members 34 may be ultrasonically bonded, heat and pressure sealed using a variety of bonding patterns, or adhesively bonded to diaper 10.

In a particular aspect of the invention, leg elastic members 34 may comprise a carrier sheet not shown to which is attached a grouped set of elastics composed of a plurality of individual, separated elastic strands. For example, the carrier sheet can comprise a strip of 0.75 mil thick, polypropylene material, and the elastic strands can be composed of Lycra elastomer available from DuPont, a business having offices in Wilmington, Del. In a preferred embodiment, each elastic strand is about 620 decitex (dtx), but strands within the range of about 470-940 dtx can also be suitable. The elastic strands are spaced about 2-4 mm apart, and can be attached to the carrier sheet with a swirl pattern of hot melt adhesive.

Absorbent structure 32 is ordinarily positioned adjacent backsheet 30 to form the various desired configurations of diaper 10. The absorbent structure is generally compressible, conformable, non-irritating to the wearer's skin, and capable of absorbing and retaining liquid body exudates. It should be understood that, for purposes of this invention, the absorbent structure can comprise a single, integral piece of material, or alternatively may comprise a plurality of individual separate pieces of material. Where the absorbent structure comprises a single, integral piece of material, as representatively shown in FIG. 2, the material can include selected structural features formed in different regions thereof. Where the absorbent structure comprises multiple pieces, the pieces may be configured as layers, or optionally, as other nonplanar shapes. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

Figure 2:
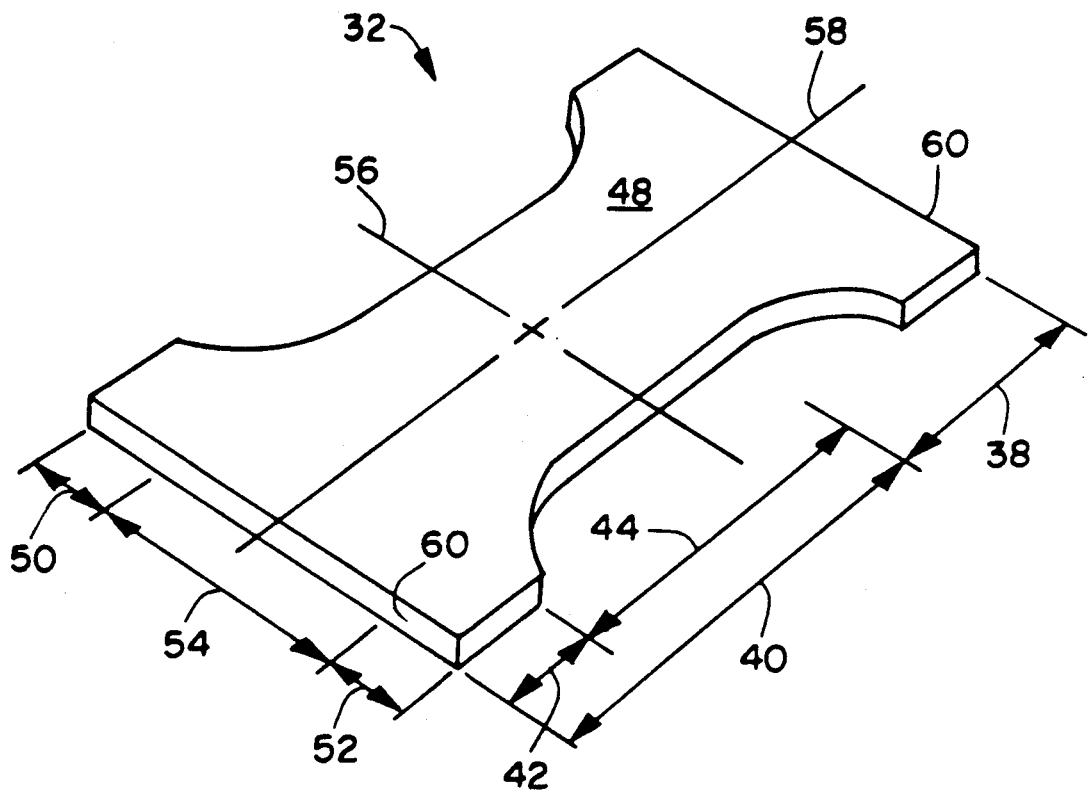
FIG. 2 representatively shows a perspective view of an absorbent structure employed in the present invention.

In the embodiment representatively shown in FIG. 2, absorbent structure 32 includes a back section 38 and a front section 40, and defines end regions 42 and target zone 44. The absorbent structure has a contoured, curvilinear periphery, particularly along its side edges. The two generally mirror-image, inwardly bowed, lateral edges provide for a narrower intermediate section suitable for positioning in the crotch of the wearer.

The absorbent structure additionally has a transverse center line 56 and a longitudinal center line 58. At least a part of bodyside liner 46 is located within target zone 44, and preferably, the bodyside liner has an areal extent which extends completely over target zone 44. Retention portion 48 is positioned in liquid communication with bodyside liner 46 to receive liquids released from the bodyside liner and transfer layer, and to hold and store the liquid. The absorbent structure may be configured with a part of retention portion 48 located within target zone 44 and the remainder of retention portion 48 located outside of the target zone. In an alternative arrangement, substantially all of the retention portion is positioned outside target zone 44. In yet another arrangement, substantially all of retention portion 48 may be positioned within target zone 44.

Front section 40 is conceptually divided into three regions comprising two transversely spaced ear regions 50 and 52 respectively, and a central region 54. Front section 40 is contiguous with back section 38, and the back and front sections of absorbent structure 32 extend away from the end edges 60 of absorbent structure 32 toward the transverse center line 56. The relative dimensions of the various sections and portions of diaper 10, and of absorbent structure 32, can be varied depending on materials used and the desired product needs. For example, front portion 40 can extend over a distance corresponding to about one-half to two-thirds, or even three-fourths of the length of absorbent structure 32. Thus, front section 40 can be constructed to encompass all of the zone of absorbent structure 32.

Front portion 40 includes an end region 42 and target zone 44. End region 42 comprises the portion of front section 40 extending a selected distance from the respective end edge 60 of absorbent structure 32 toward transverse center line 56. Target zone 44 is contiguous with end region 42 and back section 38, and encompasses the area where repeated liquid surges typically occur in absorbent structure 32. The particular location where liquid is discharged, such as during micturition, varies depending on the age and gender of the wearer. For example, male infants tend to urinate further toward the front end of the diaper. The female target zone is located closer to the center of the crotch. As a result, the shape and relative longitudinal placement of bodyside liner 46 can be selected to best correspond with the actual target zone of either or both categories of wearers.

Ear regions 50 and 52 comprise portions which generally extend from the longitudinal edges 20 of periphery 18 toward the longitudinal center line a distance from one-tenth to one-third of the overall width of absorbent structure 32, and connect to central region 54. Thus, the ear regions are configured to engage the sides of the wearer's waist and torso, and central region 54 is configured to engage the medial portion of the wearer's waist and torso. In particular embodiments of the invention, the ear regions may be absent or may be present only at one end of absorbent structure 32.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied.

Various types of wettable, hydrophilic fibrous material can be used in the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The nonwettable fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" generally describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fibers or blends of fibers used for bodyside liner 46 can be provided by a Cahn SFA-222 Surface Force Analyzer System. When measured with this system in accordance with the procedure described in detail herein below, fibers having contact angles less than 90° are referred to as "wettable", while fibers having contact angles greater than 90° are referred to as "nonwettable".

A capillary force differential or gradient created at the interfaces between bodyside liner 46, transfer layer 28 and absorbent structure 32 can advantageously improve the containment characteristics of the absorbent structure. For example, where transfer layer 28 is positioned immediately adjacent to the retention portion, and the transfer layer is appropriately configured to provide and maintain a relatively lower capillary attraction, as compared to the capillary attraction exhibited by retention portion 48, then liquid surges occurring in target zone 44 tend to be desorbed more readily from the transfer layer and into the retention portion. Because retention portion 48 can thereby have a relatively higher capillarity than transfer layer 28, the liquid surges tend to be drawn into retention portion 48 and distributed to the more remote regions thereof by wicking along the plane generally defined by the retention portion. For example, to provide for the desired difference in capillarity, transfer layer 28 and retention portion 48 can each be configured to have an effective average pore size, wherein the effective average pore size of the transfer layer is larger than the effective average pore size of the section of retention portion 48 which is immediately adjacent the transfer layer. In addition, the material of transfer layer 28 may be constructed to be less hydrophilic than the material of retention portion 48.

Similarly, where bodyside liner 46 is positioned immediately adjacent to the transfer layer 28 and the bodyside liner layer is appropriately configured to provide and maintain a relatively lower capillary attraction, as compared to the capillary attraction exhibited by transfer layer 28, then liquid surges occurring in target zone 44 tend to be desorbed more readily from the bodyside liner and into the transfer layer. As a result, the liquid surges tend to be drawn into transfer layer 28 and distributed within the transfer layer to the more remote regions thereof. To provide for the difference in capillary attraction, bodyside liner 46 and transfer layer 28 can, for example, each be configured to have an effective average pore size, wherein the effective average pore size of the bodyside liner is larger than the effective average pore size of the transfer layer. In addition, the material of bodyside liner 46 may be configured to be less hydrophilic than the material of transfer layer 28.

As representatively shown in the illustrated embodiments, retention portion 48 can be situated underlying transfer layer 28 in target zone 44, and can substantially define the boundaries of absorbent structure 32. Retention portion 48 can comprise a matrix of hydrophilic fibers, such as a web of cellulosic woodpulp fluff, mixed with highly absorbent gelling particles (e.g. superabsorbents) which have a high retention capacity even under the compressive loads applied in use. In other arrangements, retention portion 48 may comprise a mixture of the superabsorbent hydrogel-forming particles and synthetic polymer meltblown fibers, or a mixture of superabsorbent particles with a fibrous coform material comprising a blend of natural fibers and/or synthetic polymer fibers.

Suitable absorbent gelling materials can be inorganic materials such as silica gels or organic compounds such as cross-linked polymers. Cross-linking may be by covalent, ionic, Van der Waals, or hydrogen bonding. Examples of absorbent gelling polymer materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone and the like. Further polymers suitable for use in the absorbent structure include hydrolyzed, acrylonitrile grafted starch, acrylic acid grafted starch, polyacrylates and isobutylene maleic anhydride copolymers or mixtures thereof. Other suitable hydrogel-forming polymers are disclosed by Assarson et al. in U.S. Pat. No. 3,902,236 issued Aug. 26, 1975. Processes for preparing hydrogel-forming polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

As mentioned previously, the absorbent gelling material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

Examples of suitable superabsorbent materials include DOW 535, distributed by Dow Chemical Company; SANWET IM 5OOOP, distributed by Hoechst Celanese Company; and FAVOR SAB 835, distributed by Stockhausen.

Where retention portion 48 comprises a mixture of absorbent gelling particles and hydrophilic fibers, such as cellulosic fluff, the retention portion may, for example, be densified to a composite density within the range of about 0.09–0.18 grams per cubic centimeter. Preferably, the density of retention portion 48 is within the range of about 0.11–0.15 gm/cc, and more preferably, is within the range of about 0.12–0.14 gm/cc to provide improved performance.

The amount of absorbent gelling material may be about 7–16 weight percent of the retention portion. Preferably, the retention portion contains about 9–15 weight percent of the absorbent gelling material, and more preferably, contains about 11–14 weight percent of the absorbent gelling material to provide desired benefits.

The basis weight of the mixture of fibers and superabsorbent particles comprising retention portion 48 can range from about 100–1750 gsm. Preferably, the basis weight is within the range of about 500–1600 gsm, and more preferably, is within the range of about 600–1500 gsm to provide improved performance.

With reference to diaper articles, the density of retention portion 48 can be calculated from its basis weight and thickness, and is measured on newly unpacked, unfolded and desiccated diapers. For measuring bulk thickness to calculate densities, a suitable device is a TMI foam thickness gauge, Model No. TMI-49-21 or its equivalent. The apparatus is supplied by Testing Machines, Inc. of Amityville, N.Y.

Attempts to reduce gel blocking in typical fluid retention structures comprising mixtures of hydrophilic fiber and gelling material have employed a densification of such absorbent structures to ostensibly enhance the liquid wicking rate along the general plane of the structure (X-Y direction) as a result of a higher capillary force created by the smaller pore sizes within the matrix of densified fibers. Although densifying the absorbent structure can reduce the bulk thickness of the structure, the higher density may excessively reduce the rate of liquid intake. In particular, the densification of retention portion 48 may reduce the rate of liquid movement into retention portion 48 along the thickness dimension, which is the direction normal to the general X-Y plane of the article (i.e., the Z-direction).

In addition, the location of higher concentrations of absorbent gelling material in the area of desorption underneath bodyside liner 46 may create a greater gel blocking effect and thereby reduce the liquid intake rate. Accordingly, the materials in target zone 44 may optionally incorporate reduced amounts of absorbent gelling material to reduce the incidence of gel-blocking in this zone and improve the liquid intake rate. In alternative arrangements, the target zone may contain a different type of superabsorbent polymer which has a relatively slower uptake rate or even a delayed uptake rate for liquids.

Absorbent structure 32 can include a wrapsheet layer which at least partially overwraps retention portion 48. The wrapsheet may, for example, comprise a hydrophilic high wet-strength envelope web, such as a high wet strength tissue or a synthetic fibrous web, and can help minimize the migration of particles of absorbent gelling material out from retention portion 48. Such an overwrapping web can also increase the in-use integrity of the absorbent structure. The web can be glued to absorbent structure 32 and to other components of the product construction.

Bodyside liner 46 can be of any desired shape consistent with the liquid handling and absorbency requirements of absorbent structure 32. Suitable shapes include for example, circular, rectangular, triangular, trapezoidal, oblong, dog-boned, hourglass-shaped, or oval. Preferred shapes of the bodyside liner are those that increase the contacting, liquid communicating surface area between bodyside liner 46 and retention portion 48 so that the relative capillarity difference between the portions can be fully utilized. In preferred embodiments, such as shown in FIG. 1A, the bodyside liner in a newborn size diaper can be rectangular-shaped with a top surface area of about 45.6 square inches (about 294 cm$^2$).

Bodyside liner 46 should have an operable level of density and basis weight to quickly collect and temporarily hold liquid surges, and to rapidly transport the liquid from the initial entrance point to other parts of the diaper, such as transfer layer 28 and retention portion 8. Such a configuration can help prevent the liquid from pooling and collecting on the bodyside liner, and can thereby reduce the feeling of wetness by the wearer.

As illustrated in the shown embodiments, bodyside liner 46 may be positioned along the entire length of absorbent structure 32 and diaper 10. Alternatively, bodyside liner 46 may extend along only a part of the diaper length or along only a part of the length of the absorbent structure. Similarly, the bodyside liner may extend along only a part of the diaper width or along only a part of the width of the absorbent structure. For example, the bodyside liner may be shorter than absorbent structure 32 and transversely centered within the front section 40 of the absorbent structure, but offset toward the front waistband of the garment. Thus, bodyside liner 46 can be approximately centered about the longitudinal center line 58 of absorbent structure 32, and positioned primarily in the central region 54 of front section 40 of absorbent structure 32 with none of the bodyside liner 46 located in ear regions 50 and 52.

The generally forward, offset positioning of bodyside liner 46 can be defined by specifying the percentage of the top surface area of bodyside liner 46 which is found forward of a particular reference point, such as transverse centerline 24, along the length of absorbent structure 32. The positioning of bodyside liner 46 can alternatively be defined with respect to the volume of the bodyside liner positioned forward of a reference point.

It is contemplated that a bodyside liner constructed in accordance with the present invention will be tailored and adjusted to accommodate various levels of performance demand imparted during actual use. For example, mild urinary incontinence and menstrual flow pads involve different delivery rates, volumes and timing than infant urine insults. Moreover, the liquid in the surge can vary in terms of the liquid viscosity, surface tension, temperature, and other physical properties which could affect the performance of the fabric in the various actual product end usages.

With respect to absorbent articles, wherein reduced bulk or minimum cost may be important, the bodyside liner and retention portions need not take on the entire overall shape of the garment. Rather, they could be generally configured and located to cover only the genital region of the wearer. For instance, both the bodyside liner and the retention portion could be smaller than the outer cover and offset toward the front section of the garment.

It has been found that an effective fabric for constructing the bodyside liner should have a resilient structure with a selected basis weight. Such a fabric structure allows the fluid bodyside liner of the present invention to:
1. stay sufficiently open under load to maintain void volume in the fabric;
2. resist collapsing when wetted to better release liquid and to better allow the fabric to be desorbed;
3. be regenerating after being wetted to preserve void volume capacity for successive insult(s); and
4. have sufficient low-load compression to provide desired soft-cushioning and pleasing tactile feel.

The basis weight of bodyside liner 46 is at least about 15 grams per square meter, preferably is at least about 20 gsm and more preferably is at least about 24 gsm to help provide the total void volume capacity desired for effective operation. In a particular aspect of the invention the liner basis weight is not more than about 40 gsm, preferably is not more than about 30 gsm and more preferably is not more than about 29 gsm to provide desired effectiveness.

The amount of basis weight can be important for providing an overall holding capacity which is adequate to temporarily retain the amount of liquid that is typically discharged by a wearer during a single surge/insult of liquid into the absorbent article. If bodyside liner 46 and transfer layer 28 have inadequate basis weight and insufficient liquid handling capacity to adequately contain and rapidly distribute a typical amount of liquid surge, the absorbent article can exhibit excessive pooling of liquid against the wearer's skin or excessive run-off of liquid.

In one aspect of the invention, bodyside liner 46 has a dry thickness (measured at 0.1 psi) which is within the range of about 0.015–0.080 inch. Preferably, the dry thickness at 0.1 psi is within the range of about 0.028–0.075, and more preferably, the dry thickness is within the range of about 0.035–0.050 inches.

Yet another aspect of the invention comprises a structure wherein bodyside liner 46 has a wet thickness (measured at 0.1 psi) which is within the range of about 0.15–0.50 inch. Preferably, the wet thickness at 0.1 psi is within the range of about 0.020–0.050 inch, and more preferably, such wet thickness is within the range of about 0.028–0.050 inch.

A further aspect of the invention comprises a bodyside liner 46 which has a dry thickness (measured at 1.0 psi) which is within the range of about 0.004–0.030 inch. Preferably, the dry thickness at 1.0 psi is within the range of about 0.005–0.030 inch, and more preferably, such dry thickness is within the range of about 0.008–0.030 inch.

The nonwoven fibrous web of bodyside liner 46 can have a density within the range of about 0.01–0.03 g/cc (measured at 0.1 psi). The density is preferably within the range of about 0.015–0.025 g/cc, and more preferably, is within the range of about 0.018–0.022 g/cc.

Other configurations of bodyside liner 46 comprise a nonwoven fabric composed of fibers having a fiber denier within the range of about 1.0–3.0 dpf. The fiber denier is preferably within the range of about 1.5–2.5 dpf, and more preferably, is within the range of about 1.8–2.25 dpf to provide desired performance.

In a particular aspect of the invention, bodyside liner 46 is configured to provide an absorbent article which has a penetration rate index within the range of about 1.5–4.0 ml/sec. Preferably, the penetration rate is within the range of about 2.0–4.0 ml/sec, and more preferably, the penetration rate is within the range of about 2.5–4.0 ml/sec to provide improved benefits.

In another aspect of the invention, bodyside liner 46 is configured to provide an absorbent article which exhibits a Flowback index of not more than about 2.0 grams. The Flowback index is preferably not more than about 1.2 grams, and more preferably, is not more than about 0.5 grams to provide improved performance.

In a further aspect of the invention, bodyside liner 46 is configured to provide an absorbent article which has a Retention index of not more than about 0.8 grams. The Retention index is preferably not more than about 0.65 grams, and more preferably, is not more than about 0.5 grams to provide improved effectiveness.

The present invention can also be constructed to include a bodyside liner configured to provide an absorbent article which exhibits a Desorption Ratio of at least about 70. The Desorption Ratio is preferably at least about 85, and more preferably, is at least about 90 to provide improved dryness.

It will be readily apparent that absorbent articles requiring more surge handling capacity may also require proportionally greater amounts of bodyside liner material. The liner material, however, need not be of uniform basis weight throughout its areal extent, but instead can be arranged so that some sections have more surge handling material compared to other sections.

Liquid ordinarily flows along fiber surfaces, and the fiber surfaces are the usual transport routes to the void volume defined by the interfiber spacings of the fabric structure. By properly selecting the sizes, amounts and spatial arrangements of the fibers within the fabric, the liquid access to the void volume of the material can be improved without adversely affecting the liquid release characteristics.

A fabric for bodyside liner 46 can comprise a generally homogeneous blend of fine small diameter fibers intermingled with stiffer, larger diameter fibers. The finer fiber sizes can increase the available surface area per unit weight, and can improve tactile properties. Larger, stiffer fibers can enhance the ability of the material to maintain the desired structure when wetted and subjected to compressive forces, such as the compressive forces typically applied by the wearer of the garment during use, but they may adversely affect tactile properties.

The bodyside liner can be a mixture of wettable and nonwettable fibers, or can be composed entirely of wettable fibers. An appropriate fabric for the bodyside liner preferably has a sufficient amount of wettable fiber surface area to (a) initially attract liquid into the fabric structure, (b) help provide rapid fluid uptake, and (c) help fill the void volume capacity of that fabric structure.

Each incidence of liquid surge may "linger" in the fabric structure of the bodyside liner long enough to occupy at least a part of its void volume capacity, instead of simply passing through in a relatively straight-line path.

A desire to incorporate wettable fiber surface area can be met by using naturally wettable fiber components with measured contact angles of less than 90° in the fabric structure of the bodyside liner. Such fiber materials include cotton, rayon and wood pulp. Other suitable fiber materials can be inherently wettable synthetic polymers; hydrophilized or surface treated polymers, etc.; or materials having permanent, i.e, non-migratory, surface treatments applied to nonwettable substrate materials, for example, polypropylene, to reduce the contact angle below 90°.

In particularly effective embodiments of the invention, bodyside liner 46 comprises a nonwoven bonded carded web composed of bicomponent fibers, such as polyethylene/polyester conjugate fibers, polyethylene/polypropylene conjugate fibers, or the like. The components of such fibers may, for example, be configured in a side-by-side arrangement or a sheath-core arrangement. Preferred webs have the constituent fibers bonded together by a thermal process, such as through-air bonding, bonding with infrared radiation, or the like. The fibers can have a fiber denier within the range of about 1.8–3.0, and a fiber tenacity within the range of about 2.0–3.6 gpd (grams per denier). In the various embodiments of the invention, the length of the fibers can be within the range of about 1–2 in, and the fibers can be crimped with about 14–22 crimps per inch. The fibers can exhibit an elongation within the range of about 42–63%, and a boiling water shrinkage of not more about 4%. The fibers can further include a treatment/finish of about 0.2–0.8% of ethoxylated ester surfactant material.

In one aspect of the invention, body side liner 46 comprises a nonwoven bonded carded web composed of bicomponent fibers which have a core composed of polyester and a surrounding sheath composed of polyethylene. Suitable fibers are available from BASF Corporation, a business having offices located in Enka, N.C. In a preferred embodiment, the bonded carded web is formed with a through-air bonding technique, which is well known in the art. For example, through-air bonded carded webs are available from Chicopee, a business having offices located in New Brunswick, N.J. In an alternative arrangement, the bonding of the bicomponent fibrous web may be produced by an infrared bonding technique, which is also well known in the art. For example, infrared bonded carded webs are available from Bonar Fabrics, a business having offices located in Greenville, S.C.

In the illustrated embodiment of the invention, the material of bodyside liner 46 can be an infrared bonded carded web composed of polyester core, polyethylene sheath bicomponent fibers. The fabric web has a basis weight of about 0.8 osy (ounces per sq. yard), a density of about 0.027 gm/cc, and a dry thickness of about 0.30 in (measured at 0.1 psi). The fibers have a fiber denier of about 1.8 dpf, a fiber length of about 1.5 in, and have about 18 crimps per inch. The fibers further exhibit a fiber tenacity of about 2.8 gpd, a fiber elongation of about 52.5%, and a boiling water shrinkage of not more than about 2%. The fibers also include a treatment/finish of about 0.5% of ethoxylated ester surfactant.

Figure 3:
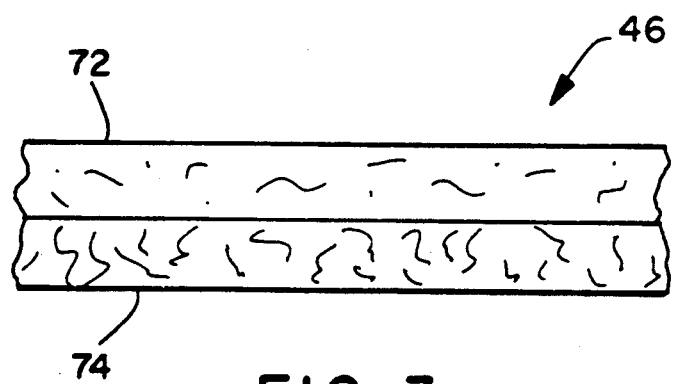
FIG. 3 representatively shows a cross-sectional view of a multilayer composite bodyside liner material.

In another aspect of the invention, body side liner 46 may comprise a multi-region composite material comprising two or more layer regions which have different configurations. The embodiment representatively shown in FIG. 3, for example, comprises an inner side layer 72 and an outer side layer 74. To form composite liner 46, the two layers are formed on top of each other and the resultant combination is subjected to thermal bonding, such as the through-air bonding or the infrared bonding described above. The thermal bonding suitably bonds the fibers within each of the inner side and outer side layers, and also interbonds the inner side layer to the outer side layer to substantially integrate the composite web.

Inwardly facing, inner side layer 72 can, for example, be composed of 1.8 denier sheath/core bicomponent fibers with a core composed of polyester (PET) and a sheath composed of polyethylene. The denier of the fibers is within the range of about 1.3-2 dpf, and the bicomponent fibrous web has a basis weight within the range of about 0.3-0.4 osy (about 10-14 gsm). An example of a suitable fiber for inner side layer 72 is a number 1051 fiber available from BASF.

Outwardly facing, outer side layer 74 can, for example, be composed of sheath/core bicomponent fibers having a core composed of polyester and a sheath composed of polyethylene. The fibers have a denier within the range of about 2.4-2.9 dpf, and the bicomponent fabric a basis weight within the range of about 0.4-0.5 osy (14-17 gsm).

The multilayer configuration of bodyside liner 46 has a composite basis weight within the range of about 23-35 gsm. Preferably, the composite basis weight is within the range of about 26-32 gsm, and more preferably, is within the range of about 28-30 gsm to provide improved performance.

The overall density of body side liner 46, whether in a single or multilayer configuration, is within the range of about 0.10-0.30 gm/cc, as measured under a restraining pressure of 0.05 psi (0.35 kPa). Preferably, body side liner 46 has a density within the range of about 0.015-0.025 gm/cc, and more preferably, has a density within the range of about 0.018-0.022 gm/cc.

FIGS. 1A-1C representatively show an embodiment of the invention wherein transfer layer 28 is generally coextensive with backsheet 30 and bodyside liner 46 has a cross-directional width which is less than the cross-directional width of the transfer layer. The bodyside liner may, for example, have a cross-directional width which is substantially coextensive with the width of the portion of absorbent structure 32 that is located at the intermediate section of diaper 10. In the illustrated embodiment, the width of bodyside liner 46 is less than the width of the intermediate section of absorbent structure 32, and the liner extends along substantially the total length of diaper 10. The bodyside liner, for example, measures approximately 3 in (about 7.62 cm) along cross-direction 17, and is placed immediately adjacent the bodyside surface of transfer layer 28 but limited to the region between the pair of containment flaps 68. Accordingly, there are portions of transfer layer 28 which are positioned laterally outboard from the containment flaps and are not covered by the bodyside liner. At such outboard regions of transfer layer 28, the transfer layer operably provides a topsheet layer of the diaper. Attachment means, such as adhesive bonds, thermal bonds or the like, may be employed to secure the placement of the bodyside liner against the transfer layer. The shown containment flaps 62 are separate members which are assembled onto transfer layer 28 and composed of a material which is different than or substantially the same as the material comprising the transfer layer. For example, the containment flaps may be constructed from a nonwoven spunbonded web composed of polypropylene fibers having about 2.5 denier and a basis weight of about 34 gsm.

Figure 4A:
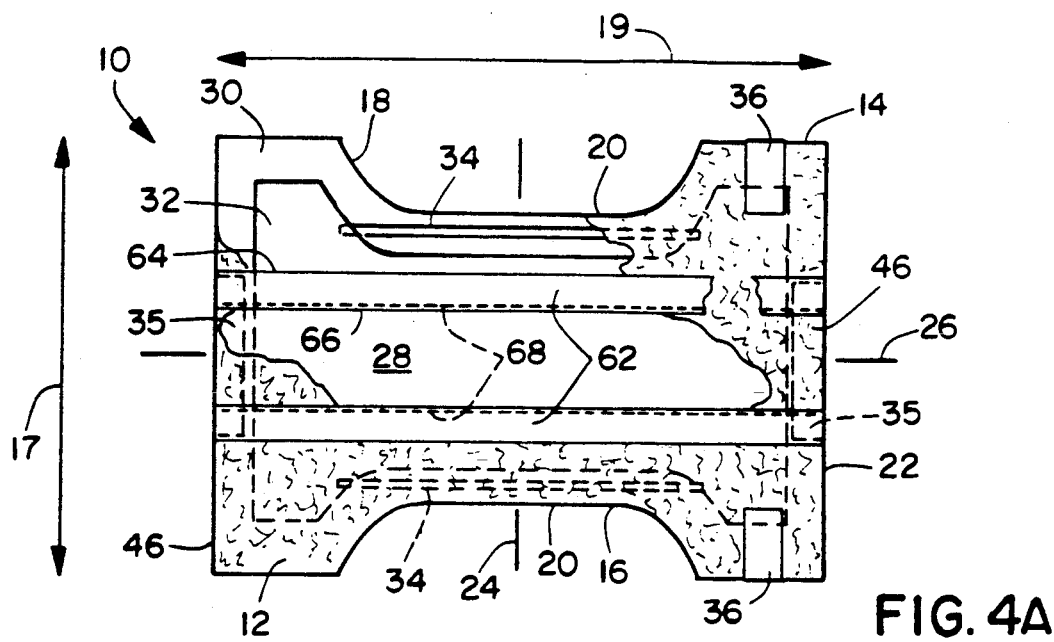
FIG. 4A representatively shows a partially cut away, top plan view of an embodiment of the invention wherein the bodyside liner is generally coextensive with the backsheet layer and the containment flaps are separate assemblies attached to the bodyside liner.
Figure 4B:
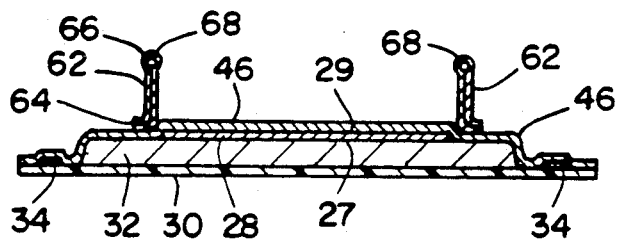
FIG. 4B representatively shows a lateral cross-sectional view of the article illustrated in FIG. 4A, wherein the elastic members at the distal edges of the containment flaps have urged sections of the flaps to a generally upright position, spaced away from the bodyside liner.
Figure 4C:
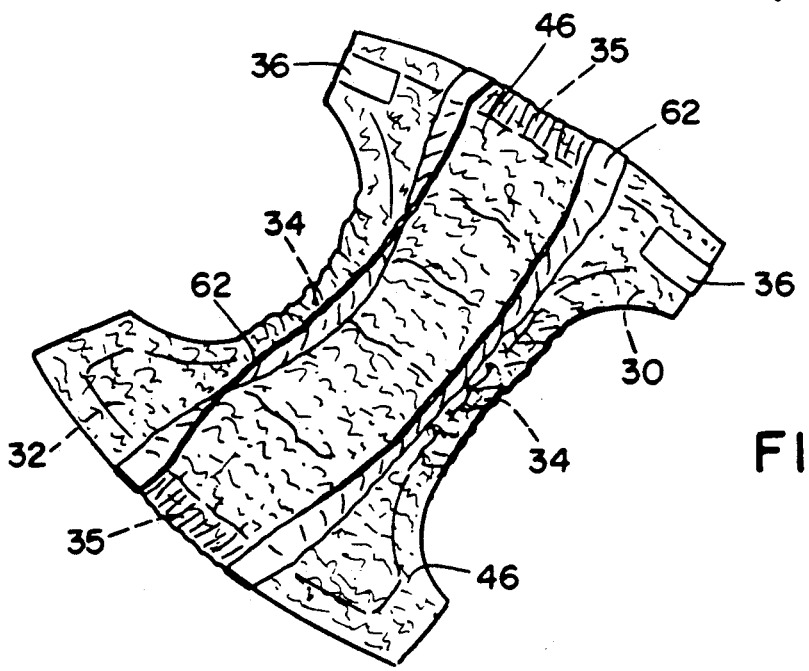
FIG. 4C representatively shows a perspective view of the article of FIG. 4A, wherein the leg elastics and flap elastics have contracted and gathered the side margins of the article and the distal edges of the containment flaps.

With reference to FIGS. 4A-4C, another optional embodiment of diaper 10 can include a bodyside liner 46 which extends across the full width of diaper 10 and is generally coextensive with backsheet 30. The transfer layer may also be substantially coextensive with the backsheet and bodyside liner. In the illustrated embodiment, however, transfer layer 28 has a width which is less than the width of bodyside liner 46. In various optional configurations, transfer layer 28 may have a length which is less than or equal to the length of bodyside liner 46. The illustrated embodiment includes containment flap members 62 which are constructed from a material which is different than the material comprising the bodyside liner. Alternatively, containment flaps 62 may be constructed from a material which is generally the same as the material comprising bodyside liner 46.

Figure 5A:
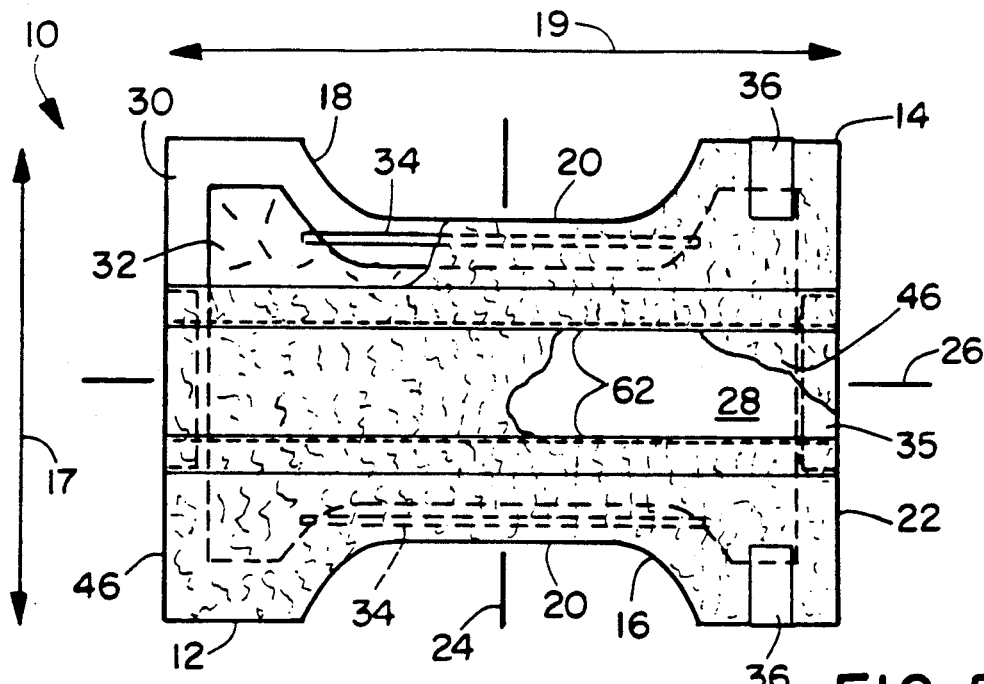
FIG. 5A representatively shows a partially cut away, top plan view of an embodiment of the invention, wherein the bodyside liner is generally coextensive with the backsheet layer and the containment flaps are integrally formed with the bodyside liner.
Figure 5B:
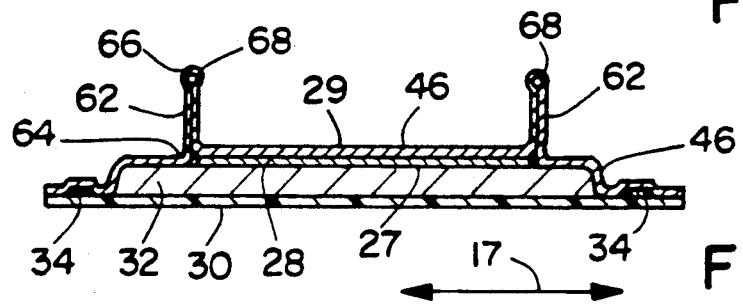
FIG. 5B representatively shows a lateral cross-sectional view of the article illustrated in FIG. 5A, wherein the elastic members at the distal edges of the containment flaps have urged sections of the flaps to a generally upright position, spaced away from the bodyside liner.
Figure 5C:
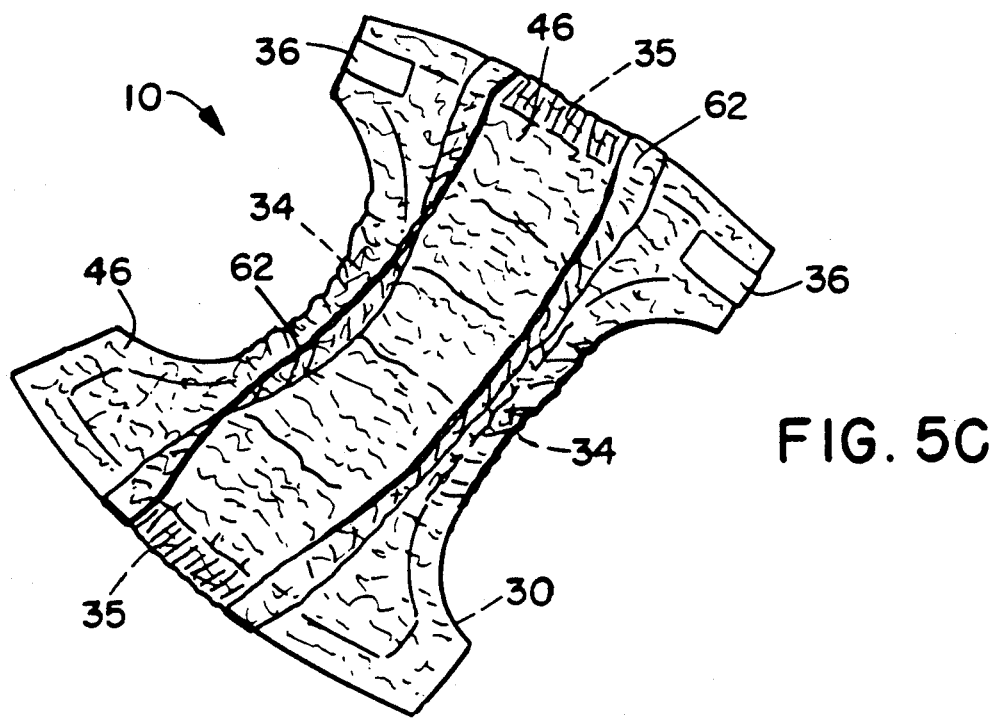
FIG. 5C representatively shows a perspective view of the article of FIG. 5A, wherein the leg elastics and flap elastics have contracted and gathered the side margins of the article and the distal edges of the containment flaps.

In particular configurations of diaper 10, such as illustrated in FIG. 4B, each containment flaps may be a separate member which is individually attached to bodyside liner 46 along fixed edge 64 of each containment flap. In other configurations of the invention, such as illustrated in FIG. 5A-5C, the containment flaps may be formed directly from and integrally with the layer of material comprising bodyside liner 46. An example of a machine technique for forming the integral containment flaps is described in U.S. Pat. No. 4,900,384; "Method and Apparatus for Making Elasticized Containment Flaps" issued Feb. 13, 1990 to Sanders et al., the disclosure of which is hereby incorporated by reference to the extent that it is consistent herewith.

Figure 6A:
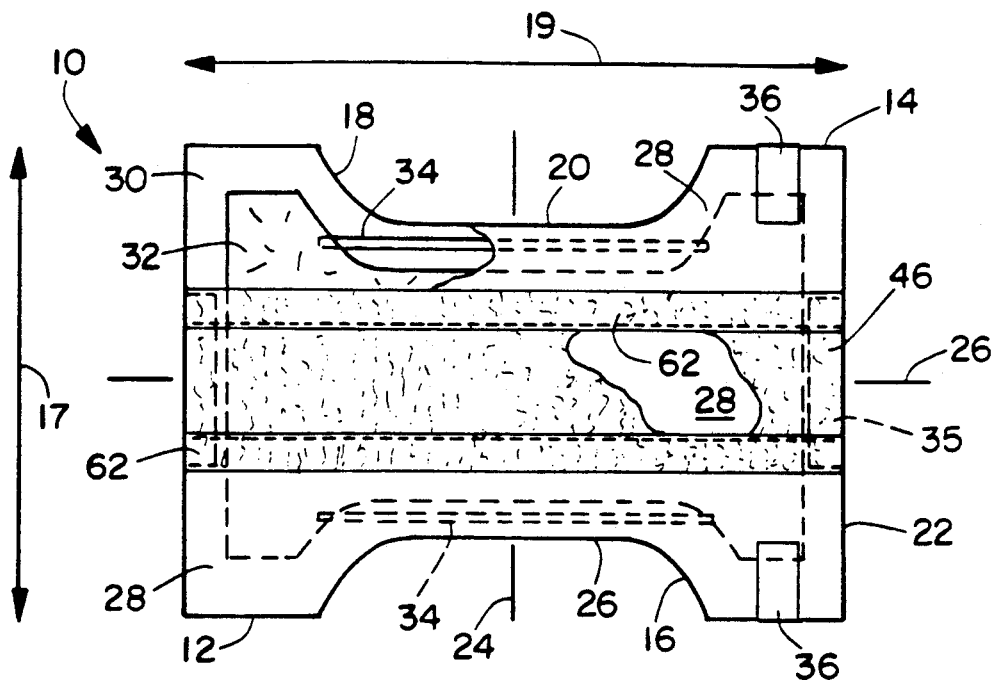
FIG. 6A representatively shows a partially cut away, top plan view of an embodiment of the invention, wherein the transfer layer/topsheet is generally coextensive with the backsheet layer, and wherein the bodyside liner has a width less than the width of the backsheet and includes containment flaps integrally formed therewith.
Figure 6B:
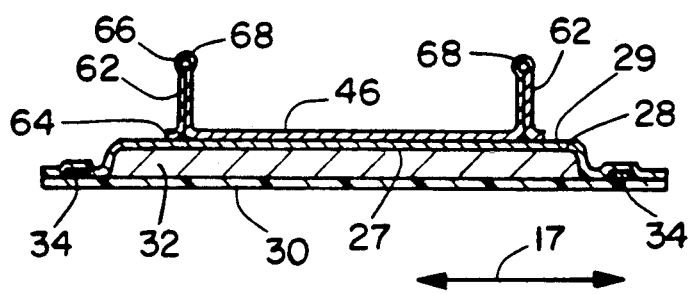
FIG. 6B representatively shows a lateral cross-sectional view of the article illustrated in FIG. 6A, wherein the elastic members at the distal edges of the containment flaps have urged sections of the flaps to a generally upright position, spaced away from the bodyside liner.
Figure 6C:
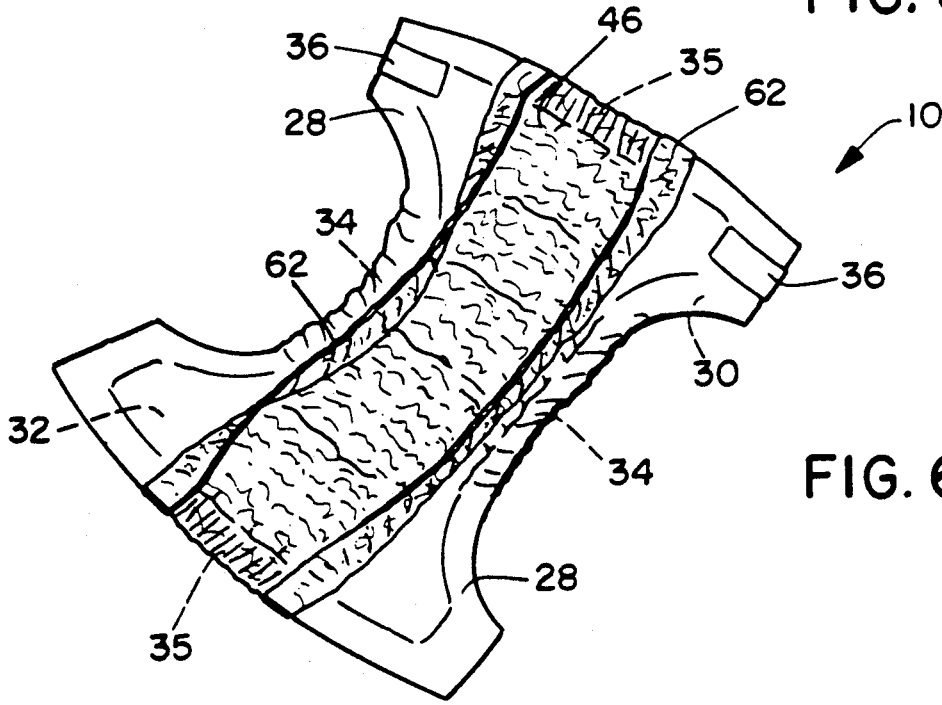
FIG. 6C representatively shows a perspective view of the article of FIG. 6A, wherein the leg elastics and flap elastics have contracted and gathered the side margins of the article and the distal edges of the containment flaps.

With reference to FIGS. 6A-6C, the invention may be configured with a transfer layer 28 which is generally coextensive with back sheet 30 and a bodyside liner layer which has a cross-directional width which is less than the cross-directional width of the transfer layer. The bodyside liner may, for example, have a cross-directional width which is substantially coextensive with the width of the portion of absorbent structure 32 that is located at the intermediate section of diaper 10.

In the illustrated embodiment, the width of bodyside liner 46 is less than the width of the intermediate section of absorbent structure 32. Containment flaps 62 may again be separate members which are assembled onto bodyside liner 46 and composed of a material which is different than or substantially the same as the material comprising the bodyside liner. Alternatively, the containment flaps may be formed integral with bodyside liner 46 from the same layer of material comprising the bodyside liner, as representatively shown in the FIG. 6B.

In the illustrated embodiments, bodyside liner 46 has a length dimension which is substantially coextensive with the length of back sheet 30. Alternatively, bodyside liner 46 may have a longitudinal length which is less than the length of the backsheet. In such configurations, bodyside liner 46 is medially positioned within diaper 10 and is spaced from one or both of the end edges of the backsheet. In the various alternative embodiments of the invention, bodyside liner 46 has a length which is about 25-100 percent of the length of backsheet 30. In a medium diaper, for example, bodyside liner 46 may comprise a patch of material measuring about 4 inches wide and about 10 inches long, which is placed in the medial section of the diaper. Preferably, the patch of bodyside liner is offset toward the front waistband of the diaper.

For the purposes of the present disclosure, the following test procedures can be used to determine particular parameters of an absorbent article.

FLUID INTAKE and FLOWBACK EVALUATION (FIFE)

Penetration Rate Index, Flowback Index and Retention Index Test

General Description:

This test has been designed to measure the absorbency/penetration time, flowback amount and amount of liquid retention in the liner of an absorbent article, such as an infant diaper. The absorbency/penetration time (in seconds) is measured by using a stopwatch and visually determining the length of time required to absorb simulated urine voidings. The flowback test measures, in grams, the amount of liquid that emerges from the "baby side" of the diaper after it has absorbed each of three liquid insults and pressure has been applied. The retention test measures, in grams, the amount of liquid that remain held in the liner component of the diaper.

Equipment & Materials:

1. FIFE Boards. See FIGS. 14A-14B and 15A-15B.

As representatively shown in FIGS. 14A and 14B, bottom FIFE board 86 includes a rectangular shaped base member 88 and a smaller, rectangular shaped platform member 90. The base member has an overall length (top to bottom of the figure) of 14 in, an overall side-to-side width of 8 in and a thickness of 0.34 in. Platform member 90 has a length of 6 in, a width of 4 in and a thickness of 0.22 in. The platform member is centered onto the top surface of base 88 and secured in place, such as by adhesive bonding. The four, peripheral top edges of platform 90 are shaped with a 0.06 inch by 45° camfer. Rectangular base 88 includes a pair of 0.5 inch diameter, cylindrical rods 94 which are press fitted into mating holes and secured in place with suitable attachment means, such as adhesive bonding. The center of each rod is positioned 0.75 in from the top, end edge of the base member, and 0.75 in from the immediately adjacent side edge of the base member. The rods extend about 1.63 in above the surface of the base member, and the uppermost exposed edges of rods 94 are rounded with a contour radius of about 0.16 inches. A series of four reference lines 96 are scribed into the top surface of base 88 and extend laterally across the width of the base member. The scribe lines are parallel and spaced from the top, end edge of base 88 by distances of 1.25 in, 1.50 in, 2.00 in and 3 in, respectively. The components of bottom FIFE board 86 are composed of a suitable water resistant material, such as Lexan plastic.

Figure 16A:
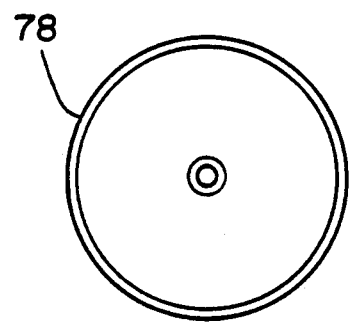
FIGS. 16A and 16B representatively show a top view and a side view, respectively, of a funnel employed for the Forced Intake and Flowback Evaluation testing.
Figure 16B:
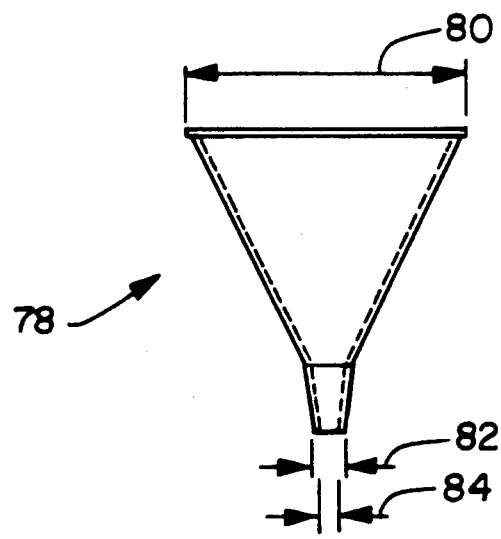

Top FIFE board 98 includes a top plate 100 and a cylindrical tube 106 which extends generally perpendicular from the plane defined by uppermost, top surface of the top plate. Top plate 100 is generally rectangular in shape and is sized with substantially the same length, width and thickness as bottom FIFE board 86. The top plate includes a pair of 0.53 inch diameter through holes 102 which are located adjacent the top edge of plate 100 and configured to slip over rods 94 in bottom FIFE board 86 to appropriately locate top FIFE board 98 in a substantially congruent, coextensive position over bottom FIFE board 86. A series of four reference lines 108 are inscribed into a top surface of plate 100 and extend linearly in the transverse direction across the width of the top plate. The scribe lines are parallel and spaced from the top, end edge of base 88 by distances of 1.25 in, 1.50 in, 2.00 in and 3 in, respectively. The medial section of top plate 100 includes a circular hole which is sized to accept the placement of cylindrical tube 106. Tube 106 has a 2.5 inch outside diameter, a 2.0 inch inside diameter and an overall length of 3.75 in. The tube is press fitted and attached in place within center hole 104 by suitable attachment means, such as adhesive bonding. Hole 104 is centered with respect to both the length and width of the top plate. Tube 106 projects generally perpendicular from the top surface 101 of plate 100 and extends through the thickness of the plate to protrude a small distance of about 0.03 inches past bottom surface 103 of plate 100. The upper, entrance edge of tube 106 has an internal camfer which generally matches the conical shape of the associated funnel representatively shown in FIG. 16. Similar to the components of bottom FIFE board 86, the components of top plate 100 are composed of a suitable water resistant material, such as Lexan plastic.

2. Four ounce Funnel; see FIGS. 16A and 16B. Funnel 78 has inlet diameter 80 of 3.25 in, a funnel throat diameter 82 of 0.438 in and a spout outlet diameter 84 of 0.25 in. The given measurements are inside diameters.

3. Saturated Capacity (SAT CAP) Tester with Magnahelic vacuum gage and latex dam: Referring to FIGS. 18A-18C, a Saturated Capacity tester vacuum apparatus 110 comprises a vacuum chamber 112 supported on four leg members 114. Vacuum chamber 112 includes a front wall member 116, a rear wall member 118 and two side walls 120 and 121. The wall members are about 0.5 in thick, and are constructed and arranged to provide a chamber having outside dimensions measuring 23.5 inches in length, 14 inches in width and 8 inches in depth. A vacuum pump (not shown) operably connects with vacuum chamber 112 through an appropriate vacuum line conduit and vacuum valve 124. In addition, a suitable air bleed line connects into vacuum chamber 112 through air bleed valve 126. A hanger assembly 128 is suitably mounted on rear wall 118 and is configured with S-curved ends to provide a convenient resting place for supporting latex dam sheet 130 in a convenient position away from the top of vacuum apparatus 110. A suitable hanger assembly can be constructed from 0.25 inch diameter stainless steel rod. Latex sheet 130 is looped around dowel member 132 to facilitate grasping and allow a convenient movement and positioning of the latex sheet. In the illustrated position, dowel member 132 is shown supported in hanger assembly 128 to position the latex sheet 130 in an open position away from the top of vacuum chamber 112. A bottom edge of latex sheet 130 is clamped against a rear edge support member 134 with suitable securing means, such as toggle clamps 140. The toggle clamps are mounted on rear wall member 118 with suitable spacers 141 which provide an appropriate orientation and alignment of the toggle clamps for the desired operation. Three support shafts 142 are 0.75 inches in diameter and are removably mounted within vacuum chamber 112 by means of support brackets 144. The support brackets are generally equally spaced along front wall member 116 and rear wall member 118 and arranged in cooperating pairs. In addition the support brackets are constructed and arranged to suitably position the uppermost portions of support shafts 142 flush with the top of the front, rear and side wall members of vacuum chamber 112. Thus, support shafts 142 are positioned substantially parallel with one another and are generally aligned with side wall members 120 and 121. In addition to rear edge support member 134, the tester apparatus includes a front support member 136 and two side support members 138 and 139. Each edge support member measures about 1 inch in width and about 1.25 inches in height. The lengths of the support members are constructed to suitably surround the periphery of the open top edges of vacuum chamber 112, and are positioned to protrude above the top edges of the chamber wall members by a distance of about 0.5 inches. A layer of egg crating type material 146 is positioned on top of support shafts 142 and the top edges of the wall members of vacuum chamber 112. The egg crate material extends over a generally rectangular area measuring 23.5 inches by 14 inches, and has a depth measurement of about 0.38 inches. The individual cells of the egg crating structure measure about 0.5 inch square, and the thin sheet material comprising the egg crating is composed of a suitable material, such as polystyrene. For example, the egg crating material can be McMaster Supply Catalog No. 162 4K 14, transluscent diffuser panel material. A layer of 0.19 mesh nylon screening 148, which measures 23.5 inches by 14 inches, is placed on top of egg crating material 146. A suitable drain line and drain valve 150 connects to bottom plate member 119 of vacuum chamber 112 to provide a convenient mechanism for draining liquids from the vacuum chamber. The various wall members and support members of tester 110 may be composed of a suitable noncorroding, moisture-resistant material, such as polycarbonate plastic. The various assembly joints may be affixed by solvent welding, and the finished assembly of the tester is constructed to be watertight. A vacuum gauge 152 operably connects through a conduit into vacuum chamber 112. A suitable pressure gauge is a Magnahelic differential gauge capable of measuring a vacuum of 0–100 inches of water, such as a No. 2100 gauge available from Dwyer Instrument Incorporated.

4. Latex dam replacement, 0.014 inch thick. Obtain from McMaster-Carr Supply Co., Chicago, Ill. 60680-4355.

5. Testing Liquid: Synthetic urine, such as synthetic urine Item No. K-C 399105 available from PPG Industries, a business having offices in Appleton, Wis.

6. Repipet capable of delivering 100±1 mL
7. Stopwatch, readable to 0.01 seconds
8. Timer
9. Graduated Cylinder, 100 mL
10. Scissors
11. Blotter paper, 120 lb, such as Verigood available from James River Corp., Neenah, Wis. 54956.
12. Balance accurate to 0.1 grams; 160 grams minimum capacity.
13. Absorbent tissue or toweling
14. FD&C Blue No. 1 dye; such as CI 42090 Brilliant Blue FCF, available from Hilton Davis Co. of Cincinnati, Ohio.
15. Paper cutter
16. Marking pen, such as "Sharpie" pen.
17. Room with standard-condition atmosphere: Temperature=23±1° C. (73.4±1.8° F.); and Relative Humidity=50±2%.

Special Instructions:

1. Record on the data sheet the type of testing liquid used. If synthetic urine is used, record the lot number and surface tension.

2. After testing is complete, rinse testing liquid from latex sheet and dry to prevent it from sticking.

3. The magnahelic gage, which measures the vacuum pressure in the Saturated Capacity Tester, may drift. It is important to this test that the pressure stays constant. Therefore, adjust the vacuum when necessary to ensure the appropriate pressure is maintained on the Magnahelic gage.

4. If the testing liquid runs off the sides when doing insults, note which insult.

Set-up Procedure:

1. Cut the blotter stock as follows to 3.0×12 inches (76.2×300 mm).

2. Prepare Dye Solution as follows:
   A. Prepare blue dye concentrate by dissolving approximately one gram of FD&C-Blue in one liter of testing liquid.
   B. Add approximately two ml of blue dye concentrate to one liter of testing liquid.

3. Calibrate the dispenser as follows
   NOTE: The dispenser must be set-up at the beginning of each day or when the setting on the repipet is changed.
   A. Fill the dispenser with the dye solution.
   B. Adjust the dispenser to the required amount of solution in accordance with the size of the diaper.

| REQUIRED AMOUNT | | |
|---|---|---|
| Small | Medium | Large/Ex. Large |
| 50 ml | 80 ml | 100 ml |

"Small"=diaper sized for use by a wearer weighing up to about 13 lbs; "Medium"=diaper sized for use by a wearer weighing from about 13 lbs up to about 23 lbs; "Large"=diaper sized for use by a wearer weighing from about 23 lbs up to about 35 lbs; "Ex. Large"=diaper sized for use by a wearer weighing more than about 35 lbs.

C. Dispense liquid several times and discard. This is to eliminate air bubbles in the line.
D. Tare the beaker on the balance.

E. Dispense the liquid into the beaker.

F. Weigh the amount of liquid in the beaker: This weight should be equal to the milliliters of liquid being dispensed. If it is not within ±0.5 grams, readjust the dispenser.

4. Preset the Vacuum Apparatus as follows:

A. Drain the excess liquid from the vacuum apparatus. (The liquid must not reach a height where it can be drawn back into the vacuum line or gauge.)

B. Close the vacuum line.

C. Open the air bleed valve.

D. Lower the latex sheet.

E. Open the vacuum line completely.

F. Slowly close the air bleed valve until the vacuum gauge reads 13.8 inches of water (0.5 psi).

Specimen Preparation:

1. Weigh each specimen to the nearest 0.1 gram and record. In addition, separately weigh the bodyside liner component of the specimen.

2. Cut any leg and waist elastics on the diaper to permit it to lie flat, making sure that the side and end "seals" around the absorbent are not disturbed.

3. Cut any containment flap elastics on the diaper to permit it to lie flat.

Figure 17C:
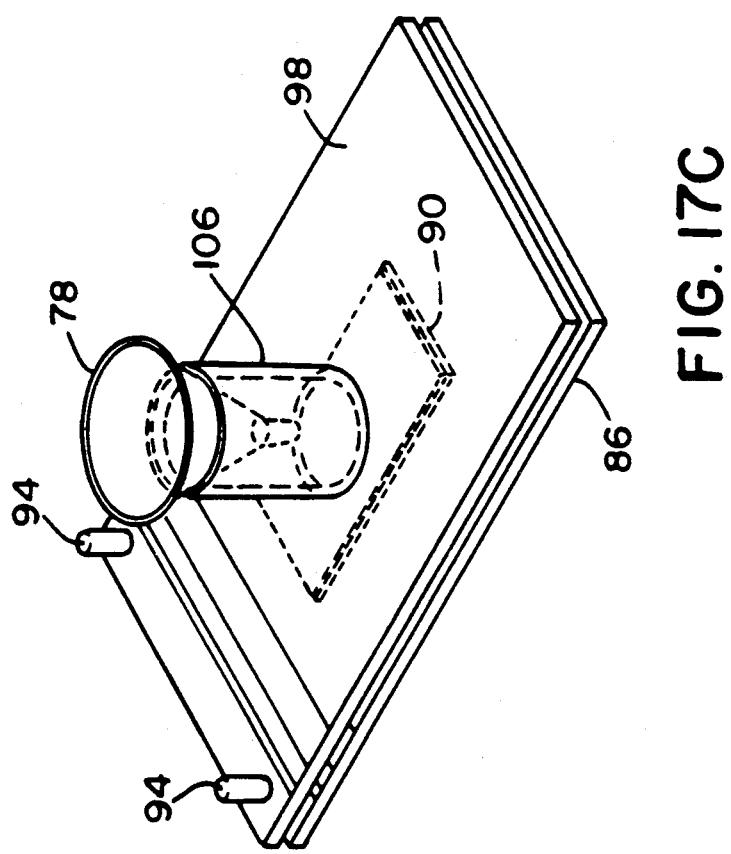
FIGS. 17A-17C representatively show a top view, a side view and a perspective view, respectively, of the bottom board, top board and funnel generally configured for use in the Forced Intake and Flowback Evaluation testing.
Figure 17A:
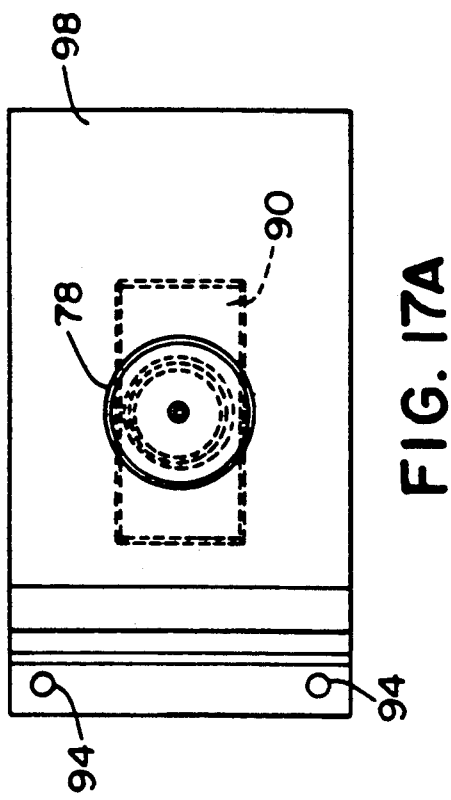
Figure 17B:
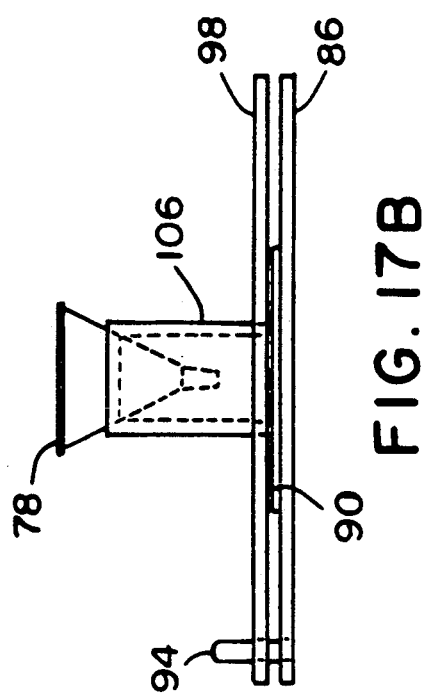

Testing Procedure: (FIGS. 17A-17C)

1. Place the specimen on the bottom FIFE board.

2. Align the specimen so the target zone is in the center of the 3×6 inch raised platform. The target zone is along the lengthwise center of the test article and is located a specific number of inches from the front edge of the fluff pad. The number of inches from the front edge of the fluff pad is determined by the size of the article, as follows:

| | TARGET ZONE AREA | | | |
|---|---|---|---|---|
| | Small | Medium | Large | Ex. Large |
| Him | 3 | 4 | 4½ | 4½ |
| Her | 4¾ | 5¾ | 6 | 6 |
| Unisex | 4 | 5 | 5½ | 5¾ |

3. Place the top FIFE board over the target, making sure there are no apparent wrinkles in the liner under the Board. Press lightly on the board to impress the cylinder ridge (on underside of board) int the specimen.

4. Place the funnel into the cylinder. The funnel must be perpendicular to the specimen and in the center of the target zone area. This is determined by sighting through the end of the funnel.

5. Measure the appropriate amount of testing liquid using the dispenser and dispense into the beaker.

6. Pour the liquid from the beaker into the funnel and onto the target area. Start the stopwatch when the liquid hits the funnel.

NOTE: Pour the liquid as fast as possible without overflowing the funnel.

7. As soon as the funnel is empty, remove it.

8. Observe the liquid intake through the cylinder top. Stop the stopwatch the moment no liquid is visible on the specimen surface.

9. Record the time to 0.01 second.

10. Using the timer, wait exactly one minute. Then repeat steps 5 through 10 for the second liquid intake.

11. Again use the timer to wait exactly one minute before doing the Flowback Test. During the one minute, tare out two blotters on the scale.

NOTE: An alternative to taring out the weight of the blotters is to weigh the blotters dry, weigh the blotters wet, and then to subtract dry weight from the wet weight to get amount of flowback.

12. One minute after the second loading, place the specimen, liner side up, on the Vacuum Apparatus. Center in the cross-direction the two tared blotters, one on top of the other, over the target zone on the specimen.

13. Cover with the rubber dam. Adjust the vacuum valve to read 13.8 inches of water (0.5 psi) on the vacuum gauge. Hold this pressure for two minutes.

14. After two minutes lift the rubber dam to release the pressure.

15. Immediately weigh the wet blotters and record the weight.

16. The amount of liquid flowback (Flowback index) is calculated as follows:

*Flowback (gm) = Wet blotter weight − Dry blotter weight.*

The value determined after the 2nd insult is reported.

17. Within one minute after the pressure is released from the specimen, repeat steps 2 through 10 for the third liquid intake time. To calculate the Penetration Rate index, divide the volume of liquid per insult (ml) by the liquid intake time (sec). The value after the 3rd insult is reported and represents the behavior of the article at the highest loading.

18. Separately weigh the bodyside liner after the 3rd insult of liquid. The amount of liquid held in the bodyside liner (Retention index) is calculated as follows:

*Retention (gm) = Wet liner weight − Dry liner weight.*

The value determined after the 3rd insult is reported.

DESORPTION INDEX TEST

The desorption ratio of a single layer material or a multi-layer material, such as a composite composed of a bodyside layer and an underlying layer, is a measure of ability of the material to readily release liquid into the retention portion of the absorbent structure. The larger the desorption ratio, the greater is the ability to release liquid. The desorption ratio can be determined as follows:

When testing an assembled absorbent article, a testing sample can be produced by cutting through the entire thickness of a selected absorbent article and removing a 2 inch by 2 inch section out from the center of the article. The liner layer is removed from the cut-out sample section, and the remaining portion of the sample section is saved. The liner layer is weighed and then immersed in a synthetic urine for one minute. A suitable synthetic urine is K-C Item No. 399105 synthetic urine product available from PPG Industries, a business located in Appleton, Wis. The sample is removed from the synthetic urine and placed on a clip for suspension in a vertical position from a ring stand, and allowed to drip for 1 minute. After this 1 min drip period, the sample and any retained liquid are weighed. The sample is then placed on a desorption pad for 2 minutes under a pressure of 3.45 kPa, which is applied over substantially the entire surface of the sample. The sample and any liquid remaining therein are weighed after the 2 min desorption period. The desorption pad is provided by the absorbent components within the previously saved, remaining portion of the sample section.

For the Desorption index testing, the desorption pad was an absorbent pad which measured 2 inches ×2 inches and was composed of a woodpulp fluff web having a basis weight of about 800 gsm and containing about 15 wt % of a superabsorbent polyacrylate, hydrogel-forming material. A suitable superabsorbent material is DOW 534, or a substantial equivalent thereof.

The desorption ratio is calculated as follows:

Desorption ratio = A/B

Where:
A = weight gain of sample after the saturation/drip process.
B = weight gain of sample after the 2 minute desorption process.

FIBER WETTABILITY DETERMINATIONS

The wettability of fibers can be determined using contact angle measurements on fibers. Repeat cycle, single fiber contact angle measurements using distilled water were performed with a Cahn Surface Force Analyzer (SFA222) and WET-TEK ® data analysis software. The SFA222 is available from Cahn Instruments, Inc., of Cerritos, Calif., and the WET-TEK software is available from Biomaterials International, Inc., of Salt Lake City, Utah. Fibers are tested through three measurement cycles, and the distilled water bath is changed between cycles one and two. Fibers are determined to be "wettable" if all three of the repeat cycles measure a contact angle of less than 90°. Otherwise, the fibers are deemed "nonwettable". The test instrument is operated in accordance with the standard operating techniques described in the Cahn SFA-222 System Instruction Manual supplied by the manufacturer.

EXAMPLES

The following examples are presented to provide a more detailed understanding of the invention. The particular materials and parameters are exemplary, and are not intended to specifically limit the scope of the invention.

EXAMPLE 1

The diaper structure of Sample 1 comprised a 1 mil thick backsheet composed of polyethylene film, and an absorbent pad. The absorbent pad included about 20 grams of wood pulp fluff and about 2.7 grams of polyacrylate superabsorbent particulate material. The superabsorbent material was DOW DRYTECH 535, or an equivalent thereof. The absorbent pad also included a wet-strength, cellulosic tissue which was placed about the mass of wood pulp fluff and superabsorbent particles. The tissue wrap had a weight of about 2.05 grams and a basis weight of about 17 gsm. The absorbent pad was sandwiched between the backsheet and a bodyside liner.

The bodyside liner material of Sample 1 was composed of a single layer, through-air bonded-carded-web composed of sheath/core bicomponent fibers. The core of the fiber was composed of polyester, and the sheath of the fiber was composed of polyethylene. The bicomponent fibers had a denier of 1.8 dpf and a fiber length within the range of about 1.4–1.6 in. The bicomponent fiber web had a basis weight of 23 gsm and had a thickness of 0.11 cm.

Figure 7:
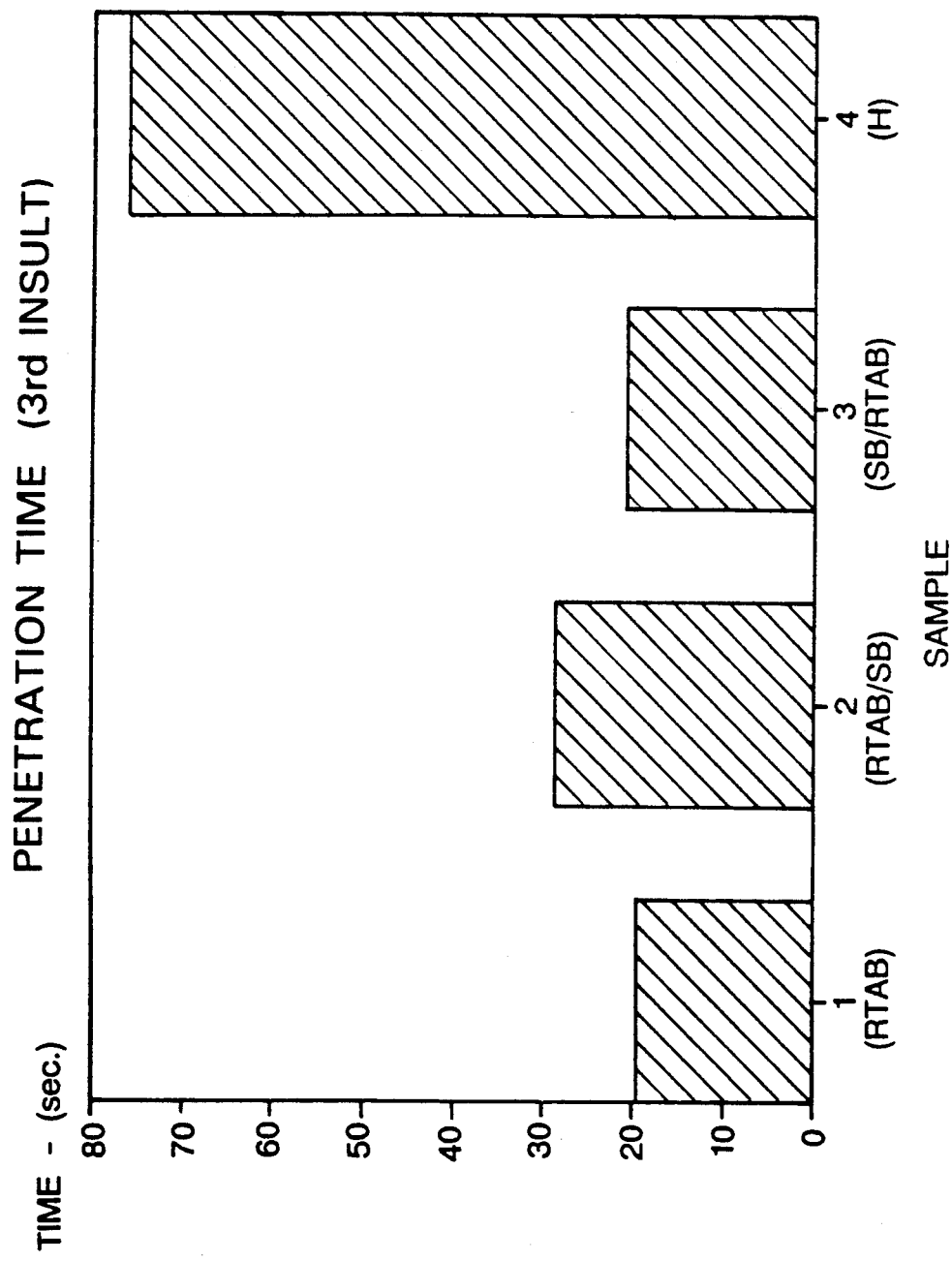
FIG. 7 is a graph which representatively shows the Penetration Rate index data for several structures.
Figure 8:
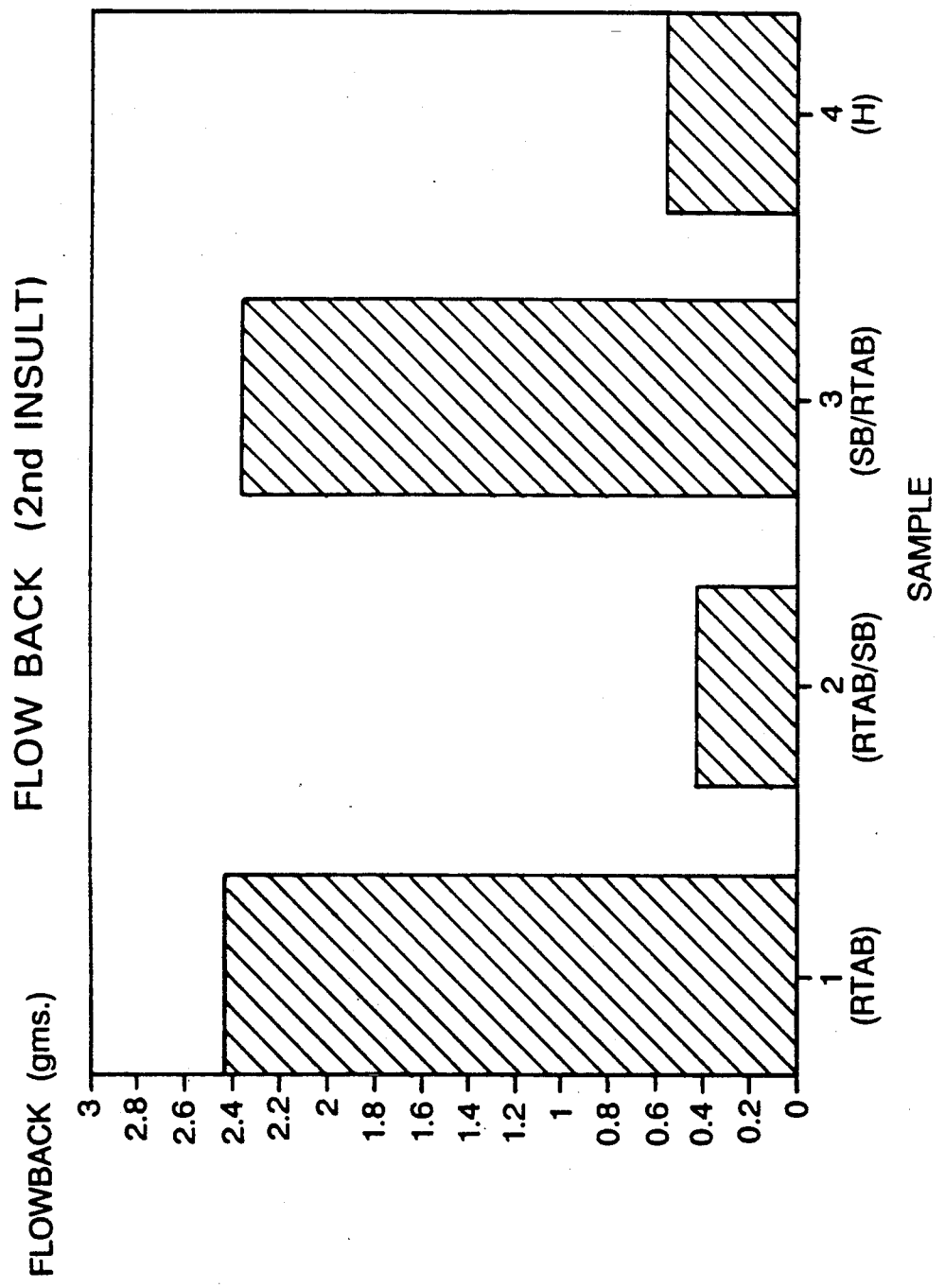
FIG. 8 is a graph which representatively shows the Flowback index data for the structures of FIG. 7.
Figure 9:
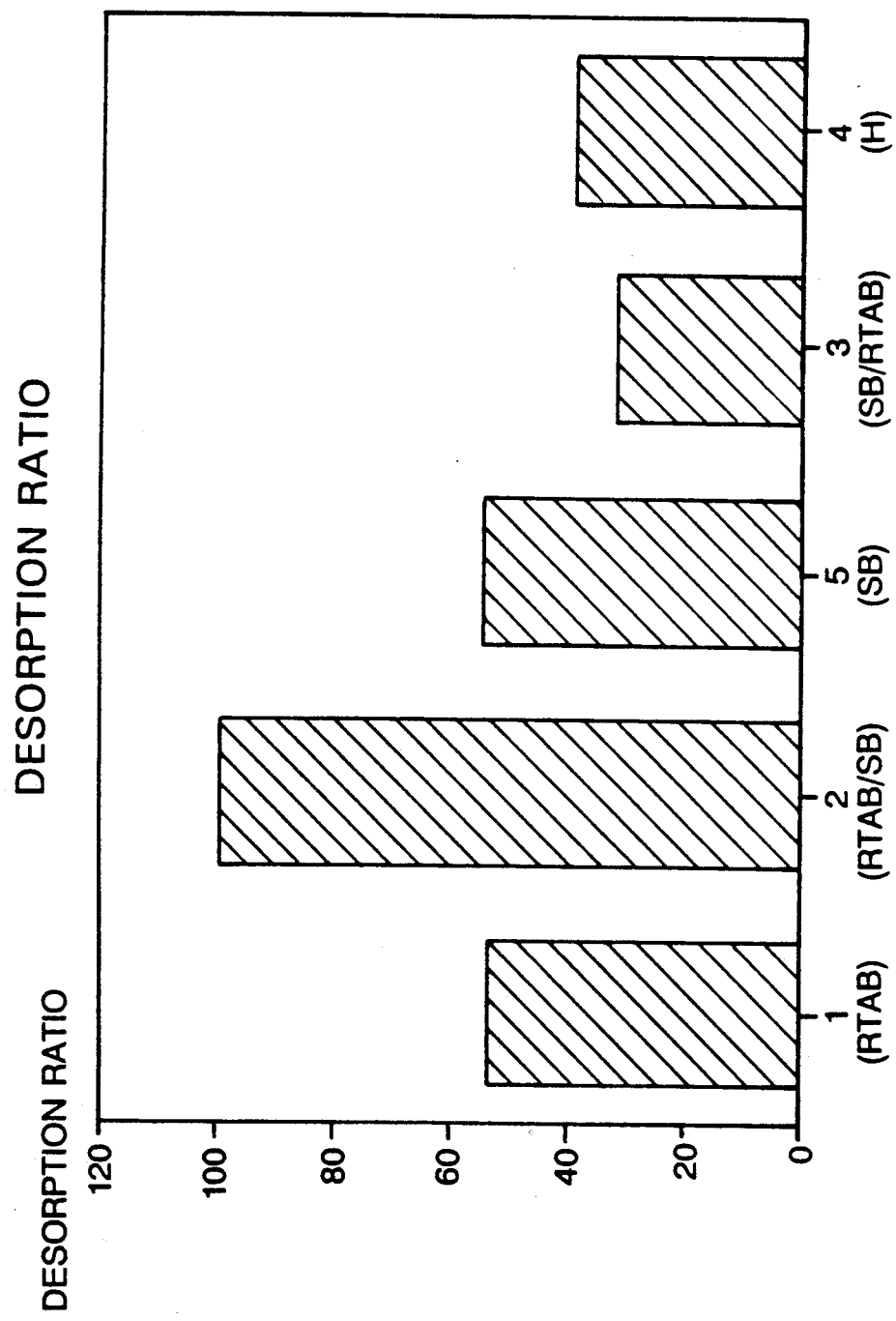
FIG. 9 is a graph which representatively shows the Desorption Ratio for several structures.

For diapers having the configuration of Sample 1, the Penetration time (3rd insult), Flowback amount (2nd insult) and Desorption Ratio are summarized in the graphs of FIGS. 7, 8 and 9, respectively.

EXAMPLE 2

The diaper structure of Sample 2 comprised a 1 mil thick backsheet composed of polyethylene film, and an absorbent pad. The absorbent pad included about 20 grams of wood pulp fluff and about 2.7 grams of polyacrylate superabsorbent particulate material. The superabsorbent material was DOW DRYTECH 835, or an equivalent thereof. The absorbent pad also included a wet-strength, cellulosic tissue which was placed about the mass of wood pulp fluff and superabsorbent particles. The tissue wrap had a weight of about 2.07 grams and a basis weight of about 17 gsm. The resultant absorbent pad was sandwiched between the backsheet and a transfer layer composed of a spunbond web of polypropylene fibers. The transfer layer material was sized to be substantially coextensive with the diaper backsheet, and was composed of polypropylene fibers having a fiber denier within the range of about 2.75–3.25d. The fibers formed a nonwoven spunbond web having a basis web of about 24 gsm and a web density of about 0.035 gm/cc. A bodyside liner, composed of a through-air bonded carded web, was attached to the bodyside surface of the transfer layer with a pattern of hotmelt adhesive applied to the end and side regions of the liner at an add-on amount of about 0.04 gm. The bodyside liner material had a width of about 3 inches and extended along the entire length of the diaper. The bodyside liner employed for Sample 2 was substantially the same as the through-air bonded-carded-web material employed to construct the bodyside liner of Sample 1.

For diapers having the configuration of Sample 2, the Penetration time (3rd insult), Flowback amount (2nd insult) and Desorption Ratio are summarized in the graphs of FIGS. 7, 8 and 9, respectively.

EXAMPLE 3

The diaper structure of Sample 3 was substantially the same as the diaper structure of Example 2, except that the relative positions of the transfer layer and bodyside liner were reversed. The bonded carded web, bodyside liner material was interposed between the absorbent pad and the transfer layer material, and the transfer layer material became the topsheet of the diaper structure.

For diapers having the configuration of Sample 3, the Penetration time (3rd insult), Flowback amount (2nd insult), and Desorption Ratio are summarized in the graphs of FIGS. 7, 8 and 9, respectively.

EXAMPLE 4

The diaper structure of Sample 4 corresponded to the structure of a commercial Huggies ® diaper, which was available in January, 1991. Sample 4 included two spunbonded layers. The bodyside layer of the diaper structure was composed of spunbonded polypropylene fibers having a denier of about 3 and perforated with a plurality of apertures having an aperture diameter of about 1 mm and an aperture density of about 74.6 apertures per square inch. The bodyside layer had a basis weight of about 24 gsm and a density of about 0.037 gm/cc. A second spunbond layer was a transfer layer interposed between the absorbent pad and the bodyside layer. The transfer layer was composed of polypropylene fibers arranged to form a web having a basis weight of about 34 gsm and a density of about 0.1 gm/cc. The transfer layer fibers had a denier of about 5, and the transfer layer web was not perforated.

For diapers having the configuration of Sample 4, the Penetration time (3rd insult), Flowback amount (2nd insult), and Desorption Ratio are summarized in the graphs of FIGS. 7, 8 and 9, respectively.

EXAMPLE 5

The diaper structure of Sample 5 was substantially the same as the diaper structure of Example 1, except that the bodyside liner material of Sample 5 was composed of a single spunbond layer constructed in accordance with the spunbond layer described with respect to Sample 2. The structure of Sample 5 provided for the Desorption Ratio shown in the graph of FIG. 9.

EXAMPLE 6

The diaper structure of Sample 6 was substantially the same as the diaper structure of Example 1, except that the bodyside liner material of Sample 6 was composed of a single layer, infrared bonded-carded-web composed of sheath/core bicomponent fibers obtained from CHICOPEE. The core of the fiber was composed of polyester, and the sheath of the fibers was composed of polypropylene. The bicomponent fibers had a denier of 1.8 dpf and a fiber length within the range of about 3.5–4.5 cm. The bonded carded web had a basis weight of 19 gsm and had a density of about 0.05 gm/cc.

Figure 10:
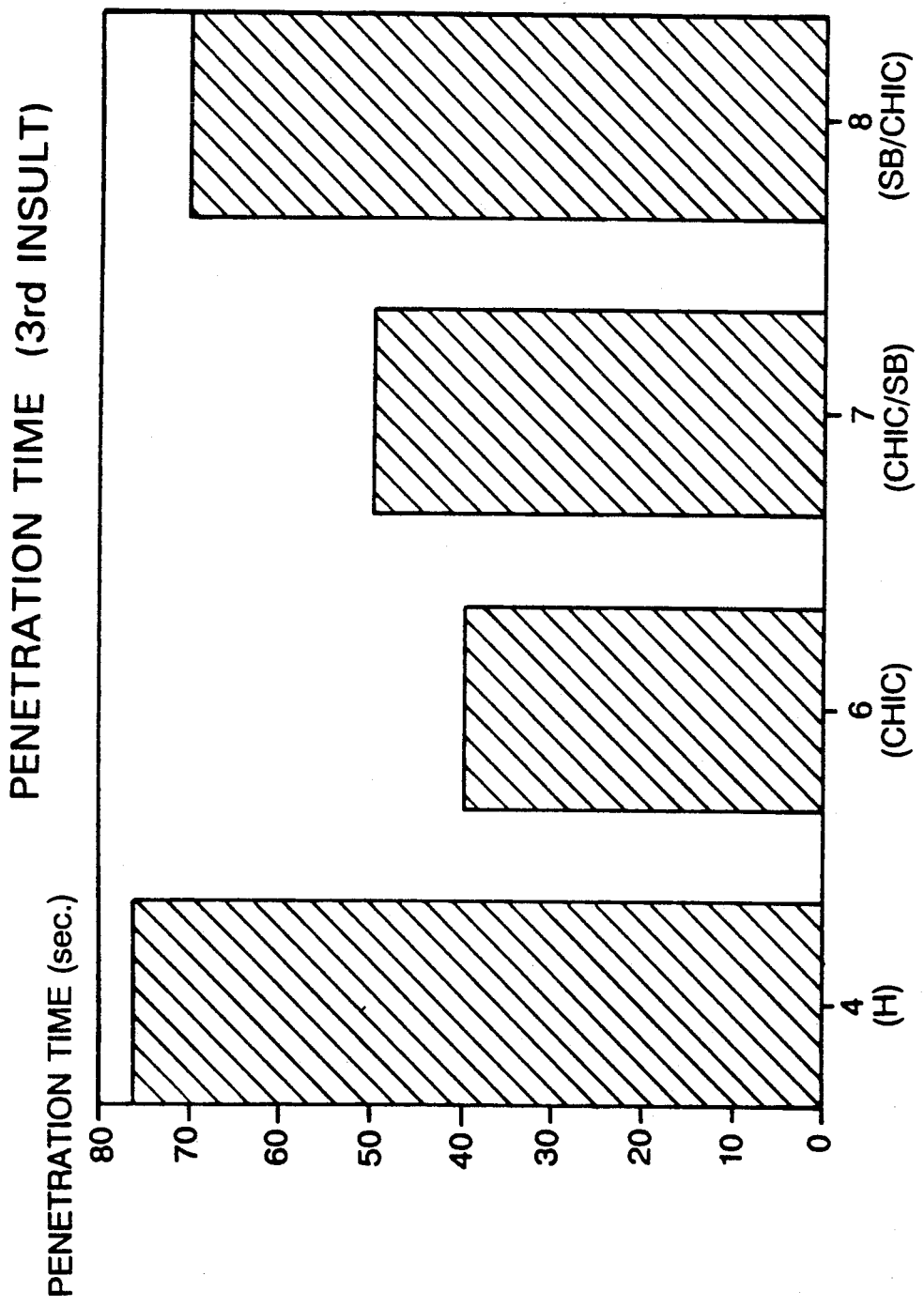
FIG. 10 is a graph which representatively shows the Penetration Rate index data for additional absorbent structures.
Figure 11:
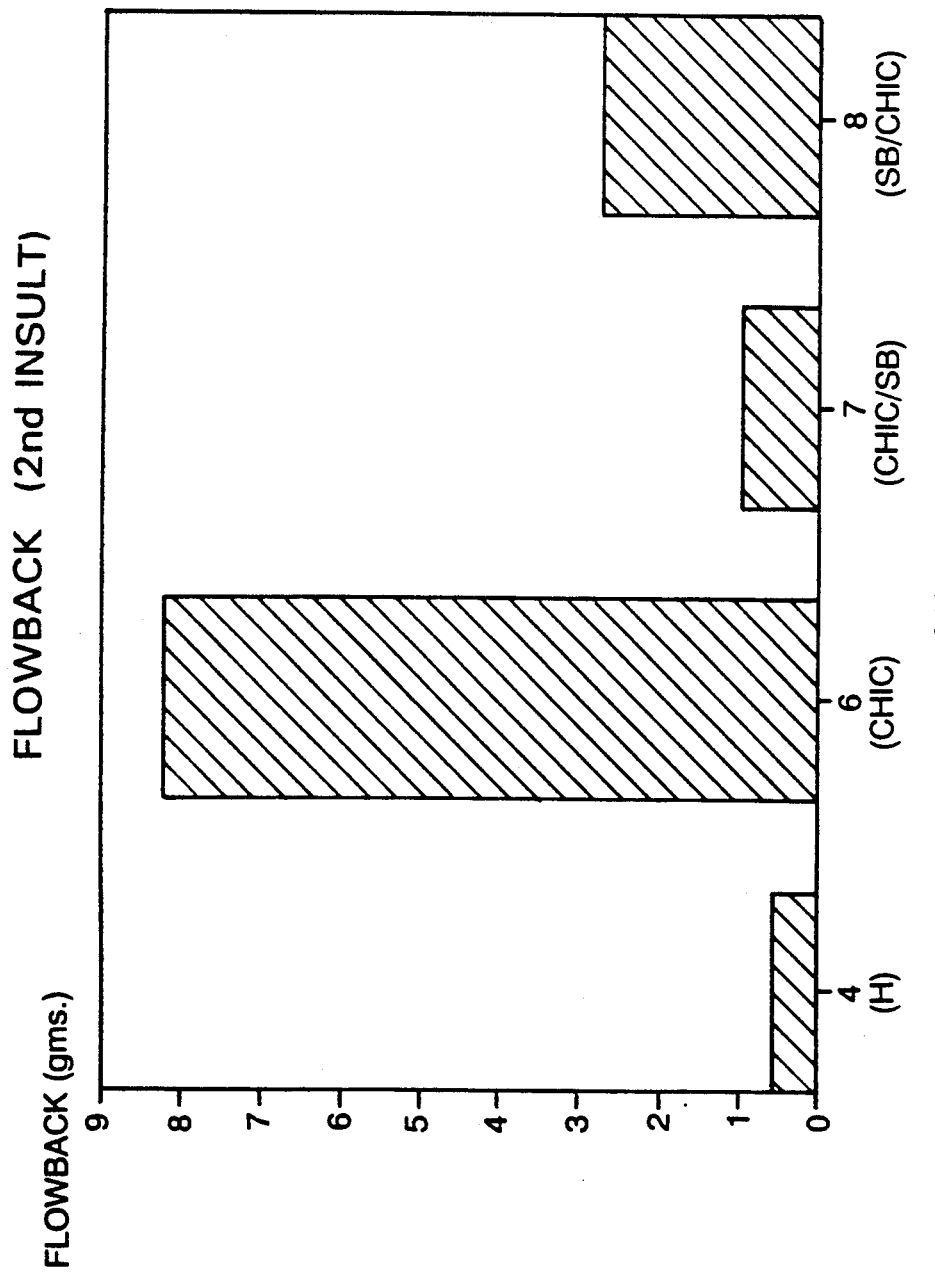
FIG. 11 is a graph which representatively shows the Flowback index data for the structures of FIG. 10.
Figure 15B:
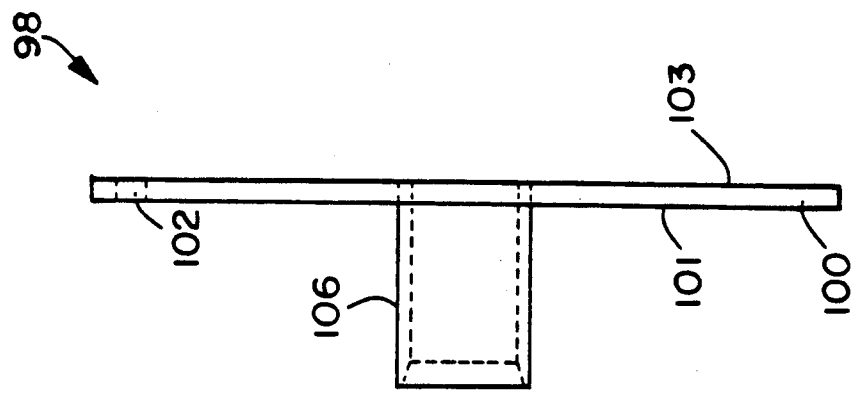
FIGS. 15A-15B representatively show a top view and a side view, respectively, of the top board employed for the Forced Intake and Flowback Evaluation testing.
Figure 15A:
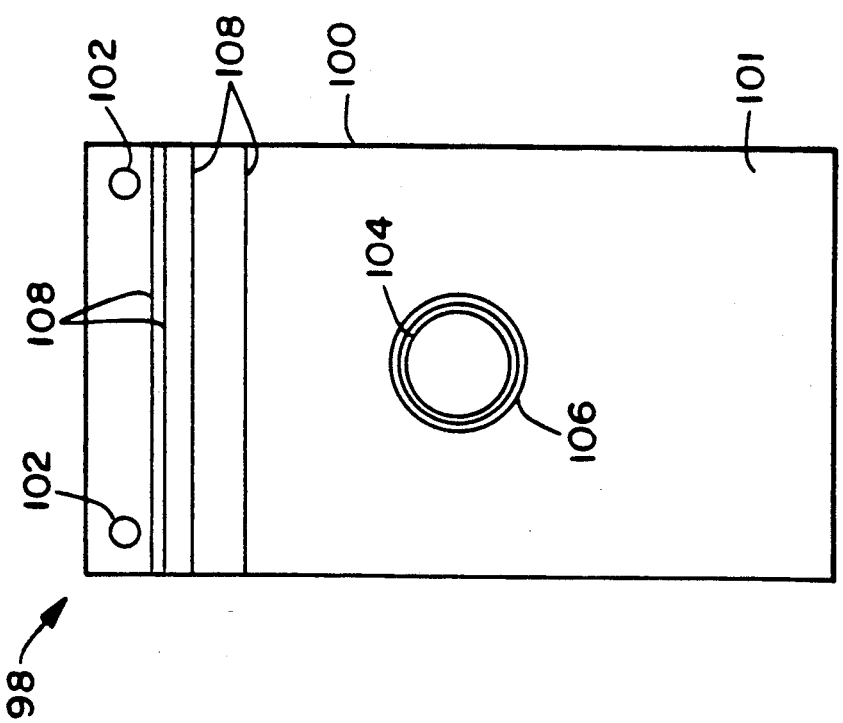

For diapers having the configuration of Sample 6, the Penetration time (3rd insult) and Flowback amount (2nd insult) are summarized in the graphs of FIGS. 10 and 11, respectively.

EXAMPLE 7

The diaper structure of Sample 7 was substantially the same as the diaper structure of Example 2, except that the through-air bonded carded web of Sample 2 was removed and replaced with the infrared bonded carded web of Sample 6.

For diapers having the configuration of Sample 7, the Penetration time (3rd insult) and Flowback amount (2nd insult) are summarized in the graphs of FIGS. 10 and 11, respectively.

EXAMPLE 8

The diaper structure of Sample 8 was substantially the same as the diaper structure of Example 7, except that the relative positions of the transfer layer and bodyside liner were reversed. The infrared bonded carded web, bodyside liner material was moved to a location interposed between the absorbent pad and the transfer layer material, and the transfer layer material became the topsheet of the diaper structure.

For diapers having the configuration of Sample 8, the Penetration time (3rd insult) and Flowback amount (2nd insult) are summarized in the graphs of FIGS. 10 and 11, respectively.

EXAMPLE 9

The diaper of Sample 9 was a small (newborn) size diaper which comprised a 1 mil thick backsheet composed of polyethylene film, and an absorbent pad. The absorbent pad included about 20 grams of wood pulp fluff and about 2.7 grams of polyacrylate superabsorbent particulate material. The superabsorbent material was DOW DRYTECH 835, or an equivalent thereof. The absorbent pad also included a wet-strength, cellulosic tissue which was placed about the mass of wood pulp fluff and superabsorbent particles. The tissue wrap had a weight of about 2.05 grams and a basis weight of about 17 gsm. The resultant absorbent pad was sandwiched between the backsheet and a transfer layer composed of a spunbond web of polypropylene fibers. The transfer layer material had a basis weight of about 0.7 osy (about 34 gsm), and was sized to be substantially coextensive with the diaper backsheet. A pair of elasticized containment flaps were positioned inboard from the leg elastics and were attached to the body side surface of the transfer layer along fixed edges of the flaps. The containment flap material was a polypropylene spunbond web having a basis weight of about 0.8 osy, and the free edges of the containment flaps were elasticized with strands of Lycra elastic having a decitex of about 470. A bodyside liner, composed of a through-air bonded carded web, was attached to the bodyside surface of the transfer layer with a swirl pattern of hotmelt adhesive applied to the end and side regions of the liner at an add-on amount of about 0.04 gm. The bodyside liner was positioned between the attached edges of the two containment flaps, and the liner fabric was composed of polyethylene/polyester, sheath-core bicomponent fibers. The bodyside liner material had a width of about 3.125 inches and extended along the entire length of the diaper. The diaper of Sample 1 also included conventional waist elastics, leg elastics, adhesive fastening tapes and a tape landing zone reinforcement patch. The various conventional components of the Sample 1 diaper were similar to the components found in a small size HUGGIES ® Supertrim Diaper which was commercially available in 1991.

The bodyside liner material of Sample 9 exhibited the characteristics set forth in Table 1 of FIGS. 12A–12B. The diaper of Sample 9 exhibited the performance parameters set forth in Table 2 of FIG. 13.

In Table 1, the term "KAWABATA" refers to a KAWABATA testing machine available from KATO TEKKO, Ltd., a business having offices in Kyoto, Japan. The KAWABATA data were generated in accordance with the instructions supplied with the KAWABATA testing machine. In accordance with the nomenclature employed by KAWABATA, the term "B" refers to bending rigidity (gf cm/cm); "G" refers to shear rigidity (gf/cm degree); "MIU" refers to coefficient of friction; "SMD" refers to geometrical roughness (micron); "T0" refers to thickness at 0 pressure; "TM" refers to thickness at maximum pressure; "RC" refers to compressional resilience (percent). For the purposes of the present disclosure, the abbreviation "MD" refers to machine direction; the direction along which the fibrous web moves through the manufacturing machine during formation. The term "CD" refers to cross direction; the direction along the web surface which is generally perpendicular to the machine direction.

EXAMPLE 10

The diaper of Sample 10 was the same as the diaper of Sample 9, except that the bodyside liner was composed of an infrared bonded carded web composed of the polyethylene/polyester sheath-core bicomponent fibers. The infrared bonded carded web was obtained from Bonar Corporation, a business having offices at Greenville, S.C. The bodyside liner material of Sample 10 had the properties set forth in Table 1 of FIG. 12. The diaper of Sample 10 had the performance parameters set forth in Table 2 of FIG. 13.

EXAMPLE 11

The diaper of Sample 11 was a small size HUGGIES® Supertrim Diaper manufactured during 1991. The diaper included an apertured bodyside liner composed of spunbond polypropylene, which was substantially coextensive with the diaper backsheet. The diaper included a pair of containment flaps connected to the bodyside liner and included a transfer layer component interposed between the absorbent pad and the bodyside liner. The transfer layer was composed of a spunbond polypropylene web having a basis web of about 24 gsm. The bodyside liner material of Sample 3 had the properties set forth in Table 1 of FIGS. 12A-12B. The diaper of Sample 3 had the parameters set forth in Table 2 of FIG. 13.

EXAMPLE 12

The diaper of Sample 12 was a small size "PAMPERS" Diaper obtained in 1991. The diaper of Sample 4 included a bodyside liner positioned immediately adjacent the absorbent pad, and did not include an intermediate layer interposed between the absorbent pad and the bodyside liner. The bodyside liner was a bonded carded web composed of polypropylene fibers. The bodyside liner material of Sample 12 had the properties listed in Table 1 of FIG. 12A-12B. The diaper of Sample 12 had the properties listed in Table 2 of FIG. 13.

EXAMPLE 13

The diaper of Sample 13 was a medium size, "ULTRAMONNY" diaper obtained during 1991. The diaper of Sample 5 included a bodyside liner positioned immediately adjacent the absorbent pad, and did not include an intermediate layer interposed between the absorbent pad and the bodyside liner. The bodyside liner was a bonded carded web composed of bicomponent polyethylene/PET fibers. The bodyside liner material of Sample 13 had the properties listed in Table 1 of FIGS. 12A-12B. The diaper of Sample 13 had the properties listed in Table 2 of FIG. 13.

EXAMPLE 14

The diaper of Sample 14 was a medium size "MAMYPOKO" diaper obtained during 1991. The diaper included a bodyside liner positioned immediately adjacent the absorbent pad, and did not include an intermediate layer interposed between the absorbent pad and the bodyside liner. The bodyside liner was a bonded carded web composed of polyethylene/polypropylene bicomponent fibers. The bodyside liner material of Sample 14 had the properties listed in Table 1 of FIGS. 12A-12B. The diaper of Sample 6 had the properties listed in Table 2 of FIG. 13.

Having thus described the invention in rather full detail, it will be readily apparent that various changes and modifications may be made without departing from the spirit of the invention. All of such changes and modifications are contemplated as being within the scope of the present invention, as defined by the subjoined claims.

We claim:

1. An absorbent article, comprising:
a backsheet layer which has length and width dimensions and which includes a front waistband section, a rear waistband section, and an intermediate section interconnecting said front and rear waistband sections;
an absorbent body which is superposed on said backsheet layer;
a liquid permeable intermediate transfer layer which is disposed in facing relation with said absorbent body to generally sandwich said absorbent body between said backsheet and transfer layer, said transfer layer having an appointed inward surface and a width dimension which is substantially coextensive with said backsheet width over at least a portion of said backsheet intermediate section; and
a liquid permeable bodyside liner layer located on said inward surface of said transfer layer, said bodyside liner having a width dimension which is less than the width of said transfer layer, said body side liner comprising a bonded carded web which has a basis weight within the range of about 15-40 gsm and is composed of bicomponent fibers having a fiber denier within the range of about 1.0-3.0, said bodyside liner constructed to provide for a Penetration Rate index of at least about 1.5 ml/sec and a Retention index of not more than about 0.8 gm.

2. An article as recited in claim 1, wherein said bodyside liner has a dry thickness (measured at 0.1 psi) which is within the range of about 0.015-0.080 in.

3. An absorbent article as recited in claim 2, wherein said bicomponent fibers have a polyester core and a polyethylene sheath around said core.

4. An absorbent article as recited in claim 2, wherein said bicomponent fibers have a polypropylene core and a polyethylene sheath around said core.

5. An article as recited in claim 1, wherein said bodyside liner is a nonwoven, bonded-carded-web composed of polyethylene/polyester bicomponent fibers, said web has a basis weight within the range of about 15-40 and a density (at 0.1 psi) within the range of about 0.01-0.03 gm/cc, and said fibers have a denier within the range of about 1-3.

6. An article as recited in claim 5, wherein said nonwoven, bonded-carded-web is composed of fibers having fiber lengths within the range of about 1-2 inches.

7. An article as recited in claim 6, wherein said bodyside liner comprises a nonwoven bonded-carded-web which includes a fibrous inner side layer and a fibrous outer side layer;
said inner side layer having a basis weight within the range of about 10-14 gsm and composed of polyethylene/polyester bicomponent fibers having a fiber denier within the range of about 1.3-2 dpf;
said bottom layer having a basis weight within the range of about 14-17 gsm, and composed of polyethylene/polyester bicomponent fibers having a fiber denier within the range of about 2.4-2.9 dpf.

8. An article as recited in claim 6, wherein said bodyside liner is a nonwoven bonded-carded-web composed of polyethylene/polypropylene bicomponent fibers, said fibers having a denier within the range of about 1-3, said web having a basis weight within the range of about 5-40 gsm and a bulk density within the range of about 0.01-0.03 gm/cc.

9. An article as recited in claim 1, wherein said bonded carded web is through-air bonded.

10. An article as recited in claim 1, wherein said bonded carded web is infrared bonded.

11. An absorbent article, comprising:
a backsheet layer which has length and width dimensions and which includes a front waistband section, a rear waistband section, and an intermediate section interconnecting said front and rear waistband sections;

an absorbent body which is superposed on said backsheet layer;

liquid permeable intermediate transfer layer which is disposed in facing relation with said absorbent body to generally sandwich said absorbent body between said backsheet and transfer layer, said transfer layer having an appointed inward surface and a width dimension which is substantially coextensive with said backsheet width over at least a portion of said backsheet intermediate section; and a liquid permeable bodyside line layer located on said inward surface of said transfer layer, wherein said bodyside liner comprises a bonded carded web which has a basis weight within the range of about 15–40 gsm and is composed of biocomponent fibers having fiber deniers within the range of about 1.0 –3.0 dpf, said bodyside liner has a width dimension which is less than said width of said transfer layer, and said bodyside liner is constructed to provide for a Penetration Rate index of at least about 1.5 ml/sec and a Flowback index of not more than about 2 gm.

12. An article as recited in claim 11, wherein said bodyside liner has a dry thickness (measured at 0.1 psi) which is within the range of about 0.015–0.080 in.

13. An absorbent article as recited in claim 12, wherein said bicomponent fibers have a polyester core and a polyethylene sheath around said core.

14. An absorbent article as recited in claim 12, wherein said bicomponent fibers have a polypropylene core and a polyethylene sheath around said core.

15. An article as recited in claim 11, wherein said bodyside liner nonwoven, bonded-carded web composed of polyethylene/polyester bicomponent fibers, said web has a basis weight within the range of about 15–40 and a density (at 0.1 psi) within the range of about 0.01–0.03 gm/cc.

16. An article as recited in claim 11, wherein said nonwoven, bonded-carded web is composed of fibers having fiber lengths within the range of about 1–2 inches.

17. An article as recited in claim 16, wherein said bodyside liner comprises a nonwoven bonded-carded-web which includes a fibrous inner side layer and a fibrous outer side layer;

said inner side layer having a basis weight within the range of about 10–14 gsm and composed of polyethylene/polyester bicomponent fibers having a fiber denier within the range of about 1.3–2 dpf;

said bottom layer having a basis weight within the range of about 14–17 gsm, and composed of polyethylene/polyester bicomponent fibers having a fiber denier within the range of about 2.4–2.9 dpf.

18. An article as recited in claim 16, wherein said body side liner is a nonwoven bonded-carded-web composed of polyethylene/polypropylene bicomponent fibers, said fibers having a denier within the range of about 1–3, said web having a basis weight within the range of about 15–40 gsm and a bulk density within the range of about 0.01–0.03 gm/cc.

19. An article as recited in claim 11, wherein said bonded carded web is through-air bonded.

20. An article as recited in claim 11, wherein said bonded carded web is infrared bonded.

21. An absorbent article, comprising:

a backsheet layer which has length and width dimensions and which includes a front waistband section, a rear waistband section, and an intermediate section interconnecting said front and rear waistband sections;

an absorbent body which is superposed on said backsheet layer;

liquid permeable intermediate transfer layer which is disposed in facing relation with said absorbent body to generally sandwich said absorbent body between said backsheet and transfer layer, said transfer layer having an appointed inward surface and a width dimension which is substantially coextensive with said backsheet width over at least a portion of said backsheet intermediate section; and a liquid permeable bodyside liner layer located on said inward surface of said transfer layer, wherein said bodyside liner comprises a bonded carded web which has a basis weight within the range of about 15–40 gsm and is composed of bicomponent fibers having fiber deniers within the range of about 1.0–3.0 dpf, said bodysided liner has a width dimension which is less than the width of said transfer layer, and said bodyside liner is constructed to provide for a Penetration Rate index of at least about 1.5 ml/sec, a Flowback index of not more than about 2 gm, a Retention index of not more than about 0.8 gm, and a Desorption index of not less than about 70.

22. An article as recited in claim 21, wherein said bodyside liner has a dry thickness (measured at 0.1 psi) which is within the range of about 0.015–0.080 in.

23. An absorbent article as recited in claim 22, wherein said bicomponent fibers have a polyester core and a polyethylene sheath around said core.

24. An absorbent article as recited in claim 22, wherein said biocomponent fibers have a polypropylene core and a polyethylene sheath around said core.

25. An article as recited in claim 21, wherein said bodyside liner is a nonwoven, bonded-carded-web composed of polyethylene/polyester bicomponent fibers, said web has a basis weight within the range of about 15–40 and a density (at 0.1 psi) within the range of about 0.01–0.03 gm/cc.

26. An article as recited in claim 21, wherein said nonwoven, bonded-carded-web is composed of fibers having fiber lengths within the range of about 1–2 inches.

27. An article as recited in claim 21, wherein said bodyside liner comprises a nonwoven bonded-carded-web which includes a fibrous inner side layer and a fibrous outer side layer;

said inner side layer having a basis weight within the range of about 10–14 gsm and composed of polyethylene/polyester bicomponent fibers having a fiber denier within the range of about 1.3–2 dpf;

said bottom layer having a basis weight within the range of about 14–17 gsm, and composed of polyethylene/polyester bicomponent fibers having a fiber denier within the range of about 2.4–2.9 dpf.

28. An article as recited in claim 21, wherein said bodyside liner is a nonwoven bonded carded-web composed of polyethylene/polypropylene bicomponent fibers, said fibers having a denier within the range of about 1–3, said web having a basis weight within the range of about 15–40 gsm and a bulk density within the range of about 0.01–0.03 gm/cc.

29. An article as recited in claim 21, wherein said bonded carded web is through-air bonded.

30. An article as recited in claim 21, wherein said bonded carded web is infrared bonded.

31. An absorbent article, comprising:
a backsheet layer which has length and width dimensions and which includes a front waistband section, a rear waistband section, and an intermediate section interconnecting said front and rear waistband sections;
an absorbent body which is superposed on said backsheet layer;
a liquid permeable intermediate transfer layer which is disposed in facing relation with said absorbent body to generally sandwich said absorbent body between said backsheet and transfer layer, said transfer layer having an appointed inward surface and a width dimension which is substantially coextensive with said backsheet width over at least a portion of said backsheet intermediate section; and
a liquid permeable bodyside liner layer located on said inward surface of said transfer layer, said bodyside liner having a width dimension which is less than the width of said transfer layer, and said bodyside liner comprising a bonded carded web which has a basis weight of about 0.8 osy and is composed of biocomponent fibers having a fiber denier of about 1.8 dpf.

32. An article as recited in claim 31, wherein said bodyside liner has a dry thickness (measured at 0.1 psi) which is within the range of about 0.015–0.080 in.

33. An absorbent article as recited in claim 32, wherein said bicomponent fibers have a polyester core and a polyethylene sheath around said core.

34. An absorbent article as recited in claim 32, wherein said bicomponent fibers have a polypropylene core and a polyethylene sheath around said core.

35. An article as recited in claim 31, wherein said bodyside liner is a nonwoven, bonded-carded-web composed of polyethylene/polyester about 15–40 and a density (at 0.1 psi) within the range of about 0.01–0.03 gm/cc.

36. An article as recited in claim 31, wherein said nonwoven, bonded-carded-web is composed of fibers having fiber lengths within the range of about 1–2 inches.

37. An article as recited in claim 31, wherein said bodyside liner comprises a nonwoven bonded-carded-web which includes a fibrous inner side layer and a fibrous outer side layer;
said inner side layer having a basis weight within the range of about 10–14 gsm and composed of polyethylene/polyester bicomponent fibers having a fiber denier within the range of about 1.3–2 dpf;
said bottom layer having a basis weight within the range of about 14–17 gsm, and composed of polyethylene/polyester bicomponent fibers having a fiber denier within the range of about 2.4–2.9 dpf.

38. An article as recited in claim 31, wherein said bonded carded web is through-air bonded.

39. An article as recited in claim 31, wherein said bonded carded web is infrared bonded.

40. An article as recited in claim 1, further comprising two containment flaps; wherein each flap has a fixed edge connected to said transfer layer and a moveable edge; said moveable edge includes an elastic member for gathering said moveable edge; and said bodyside liner is located between the fixed edges of said containment flaps.

41. An article as recited in claim 40, wherein said containment flaps are composed of the same material as said bodyside liner.

42. An absorbent article, comprising:
a backsheet layer which has length and width dimensions and which includes a front waistband section, a rear waistband section, and an intermediate section interconnecting said front and rear waistband sections;
an absorbent body which is superposed on said backsheet layer;
a liquid permeable intermediate transfer layer which is disposed in facing relation with said absorbent body to generally sandwich said absorbent body between said backsheet and transfer layer, said transfer layer having an appointed inward surface and a width dimension which is substantially coextensive with said backsheet width over at least a portion of said backsheet intermediate section; and
a liquid permeable bodyside liner layer located on said inward surface of said transfer layer, said bodyside liner comprising a nonwoven bonded carded web which has a basis weight within the range of about 15–40 gsm and includes a fibrous inner side layer and a fibrous outer side layer,
said inner side layer having a basis weight within the range of about 10–14 gsm and composed of polyethylene/polyester bicomponent fibers having a fiber denier within the range of about 1.3–2 dpf, and
said bottom layer having a basis weight within the range of about 14–17 gsm, and composed of polyethylene/polyester bicomponent fibers having a fiber denier within the range of about 2.4–2.9 dpf.

43. An article as recited in claim 42, wherein said bodyside liner is a nonwoven, bonded-carded-web composed of polyethylene/polyester bicomponent fibers, said web has a basis weight within the range of about 15–40 and a density (at 0.1 psi) within the range of about 0.01–0.03 gm/cc, and said fibers have a denier within the range of about 1–3.

44. An article as recited in claim 43, wherein said nonwoven, bonded-carded-web is composed of fibers having fiber lengths within the range of about 1–2 inches.

45. An article as recited in claim 42, further comprising two containment flaps with each flap having a fixed edge and a moveable edge, said fixed edge connected to said transfer layer with said bodyside liner located therebetween, and said moveable edge including an elastic member for gathering said moveable edge.

46. An article as recited in claim 45, wherein said containment flaps are composed of the same material as said bodyside liner.

47. An absorbent article, comprising:
a backsheet layer which has length and width dimensions and which includes a front waistband section, a rear waistband section, and an intermediate section interconnecting said front and rear waistband sections;
an absorbent body which is superposed on said backsheet layer;
a liquid permeable intermediate transfer layer which is disposed in facing relation with said absorbent body to generally sandwich said absorbent body between said backsheet and transfer layer, said transfer layer having an appointed inward surface and a width dimension which is substantially coextensive with said backsheet width over at least a portion of said backsheet intermediate section; and a liquid permeable bodyside liner layer located on said inward surface of said transfer layer, said bodyside liner having a width dimension which is less than the width of said transfer layer, said bodyside liner comprising a bonded carded web which has a basis weight within the range of about 15–40 gsm and is composed of bicomponent fibers having a fiber denier within the range of about 1.0–3.0.

48. An article as recited in claim 47, further comprising two containment flaps with each flap having a fixed edge and a moveable edge, said fixed edge connected to said bodyside liner, and said moveable edge including an elastic member for gathering said moveable edge.

49. An article as recited in claim 48, wherein said containment flaps are composed of the same material as said bodyside liner.

* * * * *

UNITED STATES PATENT AND TRADEMARK OFFICE
CERTIFICATE OF CORRECTION

PATENT NO. : 5,192,606

DATED : March 9, 1993

INVENTOR(S) : Deborah L. Proxmire, Wanda W. Jackson, Nancy D. Kollin, Tamara L. Mace, Ann L. McCormack, Daniel R. Schlinz It is certified that error appears in the above-identified patent and that said Letters Patent is hereby corrected as shown below:

IN THE SPECIFICATIONS:

Column 5, line 41, delete "4" and substitute therfor --14--.

Column 15, line 55, delete "8" and substitute therfor --48--.

Column 23, line 61, after the word "conduit" insert "154".

Signed and Sealed this

Eighteenth Day of October, 1994

Attest:

BRUCE LEHMAN

*Attesting Officer*  *Commissioner of Patents and Trademarks*